(12) United States Patent
Steege

(10) Patent No.: US 10,898,181 B2
(45) Date of Patent: Jan. 26, 2021

(54) SUTURING SYSTEM

(71) Applicant: Cypris Medical, Inc., Chicago, IL (US)

(72) Inventor: Adam T. C. Steege, Durham, NC (US)

(73) Assignee: Cypris Medical, Inc., Chicago, IL (US)

( * ) Notice: Subject to any disclaimer, the term of this patent is extended or adjusted under 35 U.S.C. 154(b) by 0 days.

(21) Appl. No.: 15/917,217

(22) Filed: Mar. 9, 2018

(65) Prior Publication Data

US 2018/0263619 A1 Sep. 20, 2018

Related U.S. Application Data

(60) Provisional application No. 62/473,271, filed on Mar. 17, 2017.

(51) Int. Cl.
*A61B 17/04* (2006.01)
*A61B 17/06* (2006.01)

(52) U.S. Cl.
CPC ...... *A61B 17/0491* (2013.01); *A61B 17/0485* (2013.01); *A61B 17/06061* (2013.01)

(58) Field of Classification Search
CPC ............ A61B 17/0469; A61B 17/0491; A61B 17/0482; A61B 17/0485; A61B 17/06061; A61B 17/0483
See application file for complete search history.

(56) References Cited

U.S. PATENT DOCUMENTS

| | | | |
|---|---|---|---|
| 3,206,217 A | 9/1965 | Shepard et al. | |
| 4,210,148 A | 7/1980 | Stivala | |
| 4,268,481 A | 5/1981 | Souvaniemi et al. | |
| 4,373,530 A | 2/1983 | Kilejian | |
| 4,841,888 A | 6/1989 | Mills et al. | |
| 4,950,283 A | 8/1990 | Dzubow et al. | |
| 5,080,663 A | 1/1992 | Mills et al. | |
| 5,507,754 A | 4/1996 | Green et al. | |
| 5,525,302 A | 6/1996 | Astle | |
| 5,549,617 A | 8/1996 | Green et al. | |
| 5,562,686 A | 10/1996 | Sauer et al. | |
| 5,766,186 A | 6/1998 | Faraz et al. | |
| 5,792,153 A | 8/1998 | Swain et al. | |
| 5,792,163 A | 8/1998 | Swain et al. | |
| 5,797,927 A | 8/1998 | Yoon | |
| 5,908,426 A | 6/1999 | Pierce | |
| 5,984,932 A | 11/1999 | Yoon | |
| 6,048,351 A | 4/2000 | Gordon et al. | |
| 6,059,800 A | 5/2000 | Hart et al. | |
| 6,077,276 A | 6/2000 | Kontos | |

(Continued)

FOREIGN PATENT DOCUMENTS

WO 2004/062466 7/2004

OTHER PUBLICATIONS

U.S. Appl. No. 62/473,271, filed Mar. 17, 2017.
(Continued)

*Primary Examiner* — Todd J Scherbel
*Assistant Examiner* — Mikail A Mannan
(74) *Attorney, Agent, or Firm* — Craig R. Miles; CR Miles P.C.

(57) ABSTRACT

A suturing system including apparatus and methods for disposing stitches in a substrate comprising a thread carrier which inserts a thread in the substrate at a first location and withdraws the thread from the substrate at a second location.

27 Claims, 19 Drawing Sheets

(56) References Cited

U.S. PATENT DOCUMENTS

| | | | |
|---|---|---|---|
| 6,155,989 | A | 12/2000 | Collins |
| 6,346,111 | B1 | 2/2002 | Gordon et al. |
| 6,464,707 | B1 | 10/2002 | Bjerken |
| 6,533,796 | B1 | 3/2003 | Sauer et al. |
| 6,936,054 | B2 | 8/2005 | Chu |
| 6,955,643 | B2 | 10/2005 | Gellman et al. |
| 6,997,931 | B2 | 2/2006 | Sauer et al. |
| 7,033,370 | B2 | 4/2006 | Gordon et al. |
| 7,060,077 | B2 | 6/2006 | Gordon et al. |
| 7,060,079 | B2 | 6/2006 | Wulc et al. |
| 7,063,710 | B2 | 6/2006 | Takamoto et al. |
| 7,175,636 | B2 | 2/2007 | Yamamoto et al. |
| 7,220,266 | B2 | 5/2007 | Gambale |
| 7,399,304 | B2 | 7/2008 | Gambale et al. |
| 7,442,198 | B2 | 10/2008 | Gellman et al. |
| 7,517,356 | B2 | 4/2009 | Heinrich |
| 7,731,727 | B2 | 1/2010 | Sauer |
| 7,763,036 | B2 | 7/2010 | Stokes et al. |
| 7,780,684 | B2 | 8/2010 | Wulc et al. |
| 7,833,236 | B2 | 11/2010 | Stokes et al. |
| 7,846,169 | B2 | 12/2010 | Shelton, IV et al. |
| 7,951,157 | B2 | 5/2011 | Gambale |
| 8,057,386 | B2 | 11/2011 | Azonian et al. |
| 8,075,573 | B2 | 12/2011 | Gambale et al. |
| 8,100,920 | B2 | 1/2012 | Gambale et al. |
| 8,177,794 | B2 | 5/2012 | Cabrera et al. |
| 8,177,797 | B2 | 5/2012 | Shimoji et al. |
| 8,206,284 | B2 | 6/2012 | Azonian et al. |
| 8,226,665 | B2 | 7/2012 | Cohen |
| 8,246,637 | B2 | 8/2012 | Viola et al. |
| 8,257,369 | B2 | 9/2012 | Gellman et al. |
| 8,286,847 | B2 | 10/2012 | Taylor |
| 8,292,886 | B2 | 10/2012 | Kerr et al. |
| 8,292,905 | B2 | 10/2012 | Taylor et al. |
| 8,292,906 | B2 | 10/2012 | Taylor et al. |
| 8,313,509 | B2 | 11/2012 | Kostrzewski |
| 8,337,515 | B2 | 12/2012 | Viola et al. |
| 8,372,090 | B2 | 2/2013 | Wingardner et al. |
| 8,403,837 | B2 | 3/2013 | Okoniewski |
| 8,413,869 | B2 | 4/2013 | Heinrich |
| 8,465,499 | B2 | 6/2013 | Onuki et al. |
| 8,475,453 | B2 | 7/2013 | Marczyk et al. |
| 8,490,851 | B2 | 7/2013 | Blier et al. |
| 8,496,674 | B2 | 7/2013 | Cabrera et al. |
| 8,506,581 | B2 | 8/2013 | Wingardner, III et al. |
| 8,628,545 | B2 | 1/2014 | Cabrera et al. |
| 8,636,752 | B2 | 1/2014 | Cabrera et al. |
| 8,641,729 | B2 | 2/2014 | Filipi et al. |
| 8,721,640 | B2 | 5/2014 | Taylor et al. |
| 8,747,424 | B2 | 6/2014 | Taylor et al. |
| 8,882,785 | B2 | 11/2014 | DiCesare et al. |
| 8,906,041 | B2 | 12/2014 | Chu |
| 8,968,339 | B2 | 3/2015 | Malkowski |
| 8,968,340 | B2 | 3/2015 | Chowaniec et al. |
| 8,968,342 | B2 | 3/2015 | Wingardner, III et al. |
| 9,113,860 | B2 | 8/2015 | Viola et al. |
| 9,149,270 | B2 | 10/2015 | Fogel |
| 9,204,924 | B2 | 12/2015 | Marczyk et al. |
| 9,326,770 | B2 | 5/2016 | Shelton, IV et al. |
| 9,504,465 | B2 | 11/2016 | Chu |
| 2002/0119177 | A1 | 8/2002 | Bowman et al. |
| 2003/0208209 | A1 | 11/2003 | Gambale et al. |
| 2004/0015177 | A1 | 1/2004 | Chu |
| 2004/0034371 | A1 | 2/2004 | Lehman et al. |
| 2004/0236353 | A1 | 11/2004 | Bain et al. |
| 2005/0251153 | A1 | 11/2005 | Sakamoto et al. |
| 2006/0036232 | A1 | 2/2006 | Primavera et al. |
| 2006/0085016 | A1 | 4/2006 | Eremia |
| 2008/0147096 | A1 | 6/2008 | Azonian et al. |
| 2009/0018580 | A1 | 1/2009 | Wulc |
| 2010/0016868 | A1 | 1/2010 | Kim |
| 2010/0137888 | A1 | 6/2010 | Wulc et al. |
| 2010/0249498 | A1 | 9/2010 | Wingardner et al. |
| 2011/0082347 | A1 | 4/2011 | Okoniewski |
| 2012/0029536 | A1 | 2/2012 | Dicesare et al. |
| 2012/0215235 | A1 | 8/2012 | Fogel |
| 2013/0035688 | A1 | 2/2013 | Kerr et al. |
| 2013/0172685 | A1 | 7/2013 | Okoniewski |
| 2014/0012292 | A1* | 1/2014 | Stewart ............ A61B 17/0483 606/148 |
| 2014/0114309 | A1 | 4/2014 | Payne et al. |
| 2014/0163375 | A1 | 6/2014 | Wasielewski |
| 2014/0371760 | A1 | 12/2014 | Menn |
| 2016/0338691 | A1 | 11/2016 | Weber et al. |

OTHER PUBLICATIONS

PCT International Patent Application No. PCT/US18/21942, filed Mar. 12, 2018.

PCT International Patent Application No. PCT/US18/21942; International Search Report and Written Opinion of the International Searching Authority dated May 24, 2018, 13 pages.

U.S. Appl. No. 15/947,612, filed Apr. 6, 2018.

PCT International Patent Application No. PCT/US18/27173, filed Apr. 11, 2018.

Covidien. SILS™ Stitch Articulating Suturing Device. Product Sheet, www.covidiet.com, originally downloaded Jan. 6, 2016, 2 pages.

Covidien. V-Loc™ Wound Closure Reload for Use With Endo Stitch™ and SILS™ Stitch Suturing Devices. Product Sheet, www.covidiet.com, originally downloaded Jan. 6, 2016, 28 pages.

Eremia et al. Novel Face-Lift Suspension Suture and Inserting Instrument: Use of Large Anchors Knotted into a Suture with Attached Needle and Inserting Device Allowing for Single Entry Point Placement of Suspension Suture. Preliminary Report of 20 Cases with 6-to 12-Month Follow-Up. Dermatol Surg., Mart 2006, 32(3):335-45.

PCT International Patent Application No. PCT/US07/21449, filed Oct. 5, 2007.

U.S. Appl. No. 60/958,474, filed Jul. 6, 2007.
U.S. Appl. No. 60/923,980, filed Apr. 17, 2007.
U.S. Appl. No. 60/923,804, filed Apr. 16, 2007.
U.S. Appl. No. 60/849,561, filed Oct. 5, 2006.
U.S. Appl. No. 60/849,508, filed Oct. 5, 2006.
U.S. Appl. No. 60/849,562, filed Oct. 5, 2006.

PCT International Patent Application No. PCT/US18/37406; International Search Report and Written Opinion of the International Searching Authority dated Sep. 13, 2018, 10 pages.

PCT International Patent Application No. PCT/US18/27173; International Search Report and Written Opinion of the International Searching Authority dated Jun. 29, 2018, 8 pages.

U.S. Appl. No. 15/947,612; Office Action dated Dec. 11, 2019.
U.S. Appl. No. 15/947,612; Office Action dated Jan. 14, 2020.
U.S. Appl. No. 16/734,121, filed Jan. 3, 2020.
U.S. Appl. No. 15/994,932; Office Action dated Jul. 21, 2020.
U.S. Appl. No. 15/994,932, Office Action dated Mar. 4, 2020.

* cited by examiner

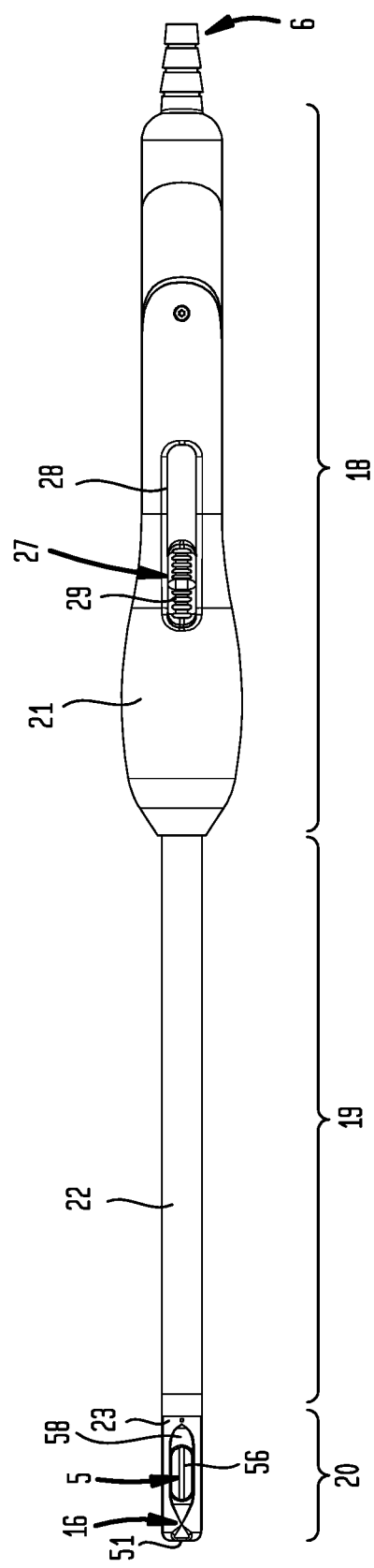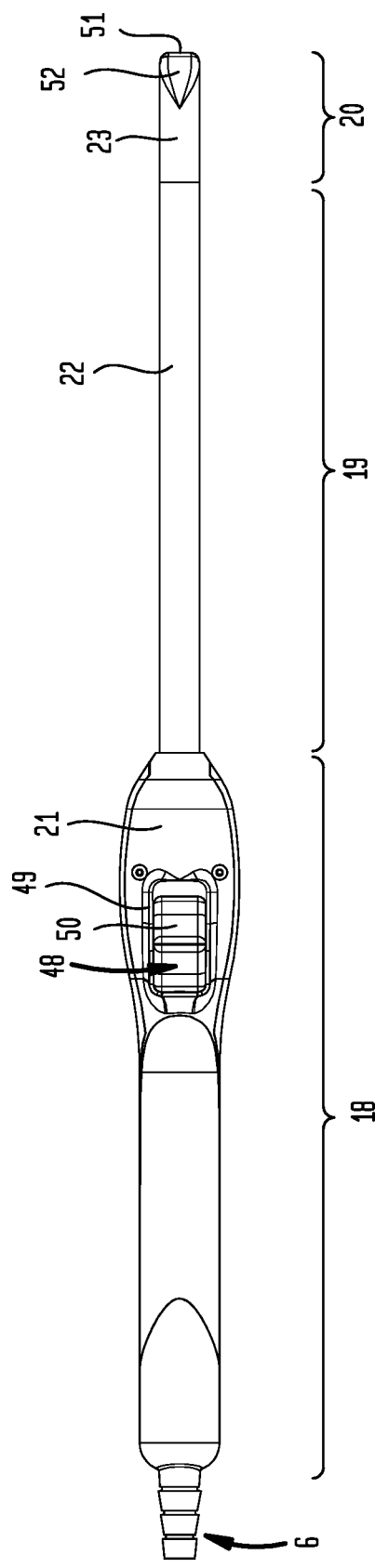

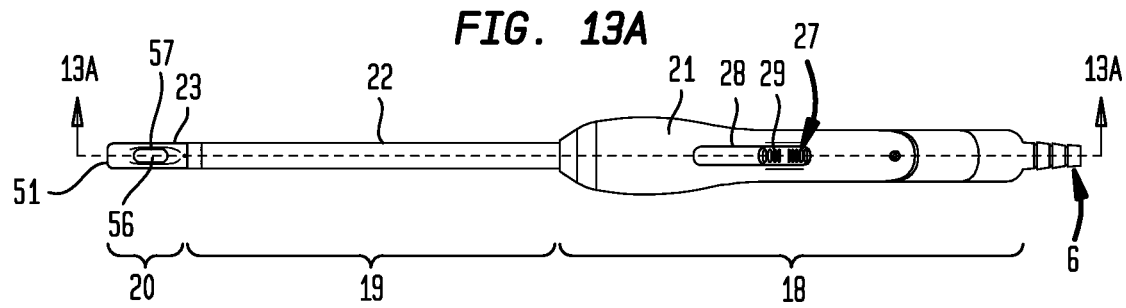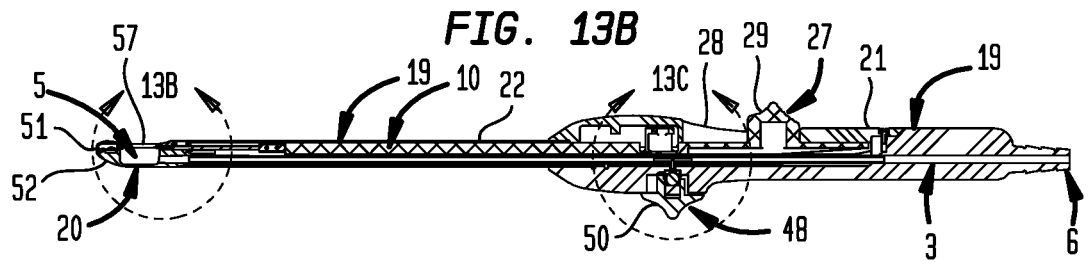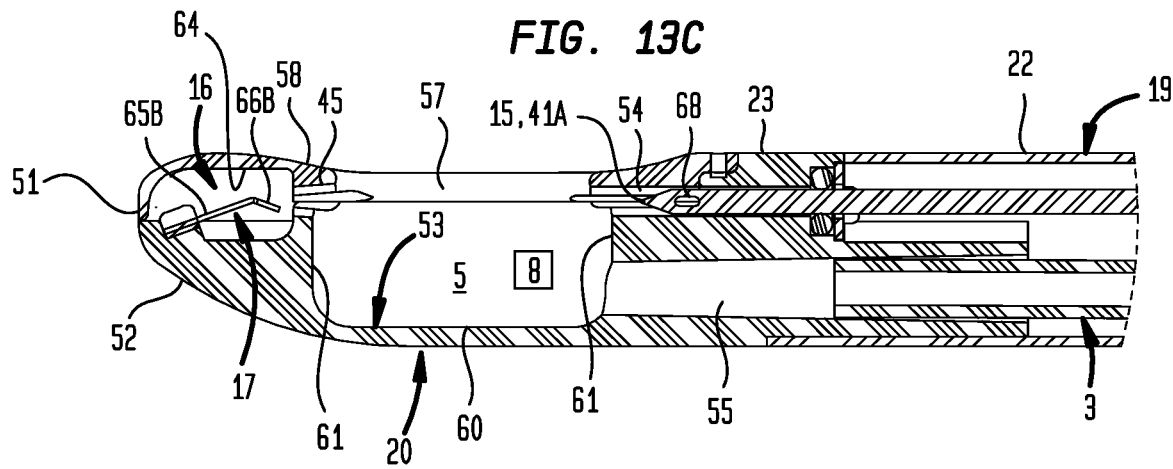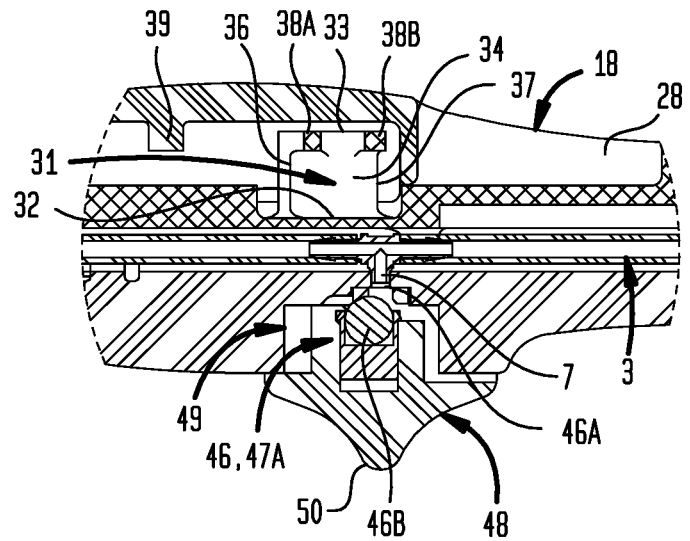

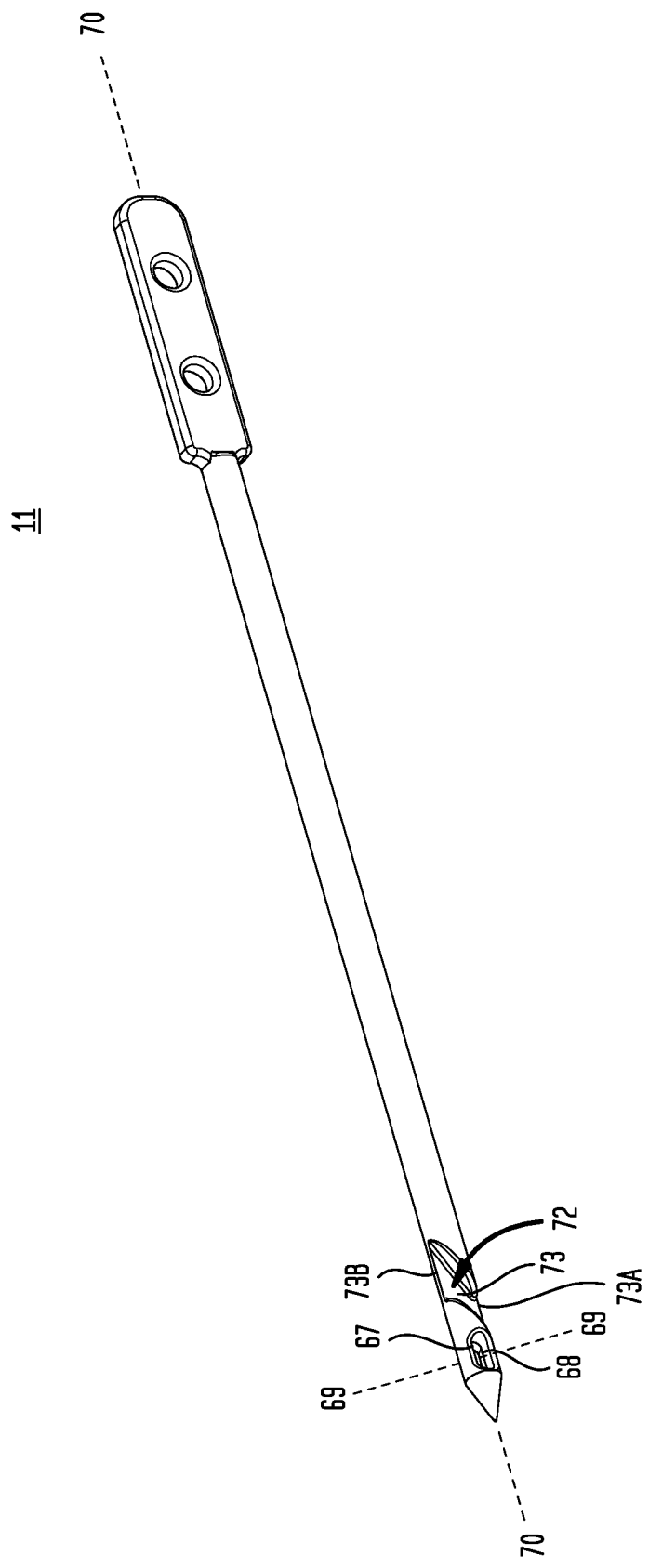

SUTURING SYSTEM

This United States Non-Provisional Patent Application claims the benefit of U.S. Provisional Patent Application No. 62/473,271, filed Mar. 17, 2017, hereby incorporated by reference herein.

I. BACKGROUND

A suturing system including apparatus and methods for disposing stitches in a substrate comprising a thread carrier which inserts a thread in the substrate at a first location and withdraws the thread from the substrate at a second location.

II. SUMMARY OF THE INVENTION

A suturing apparatus including one or more of: a housing which maintains in operable relation a valved conduit operable to regulate fluid flow between a substrate capture chamber and a vacuum port or an ambient pressure port to regulate pressure within the substrate capture chamber in relation to the ambient pressure surrounding the substrate capture chamber and a thread carrier driver disposed to axially move a thread carrier carrying a thread between a retracted condition disposing the thread carrier outside of the substrate capture chamber and an extended condition in which a thread carrier terminal end of the thread carrier passes axially through the substrate capture chamber into a thread capture chamber to engage a thread capture assembly which captures the thread to generate a thread loop upon return of the thread carrier toward the retracted condition.

Naturally, further objects of the invention are disclosed throughout other areas of the specification, drawings, photographs, and claims.

III. A BRIEF DESCRIPTION OF THE DRAWINGS

FIG. 9 is a top plan view of a particular embodiment of the suturing apparatus.

FIG. 10 is a bottom plan view of a particular embodiment of the suturing apparatus.

FIG. 13A is a top plan view of a particular embodiment of the suturing apparatus depicting the location of cross section 13A-13A.

FIG. 13B is a cross section view 13A-13A as shown in FIG. 13.

FIG. 13C is an enlarged view of portion 13B shown in FIG. 13A which depicts the thread carrier in a first thread carrier position retracted within the handle outside of the substrate capture chamber.

FIG. 13D is an enlarged view of portion 13C shown in FIG. 13A having the ambient pressure port in the open condition.

FIG. 16 is perspective view of a particular embodiment of the thread carrier.

Figure 22A:
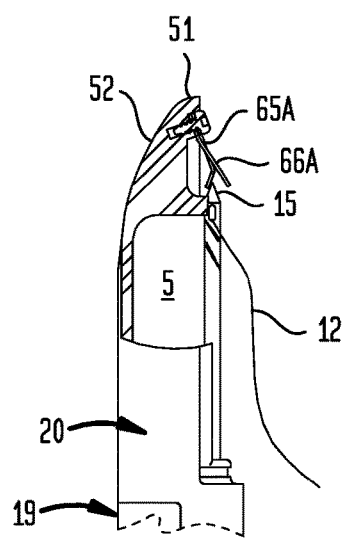
Figure 24A:
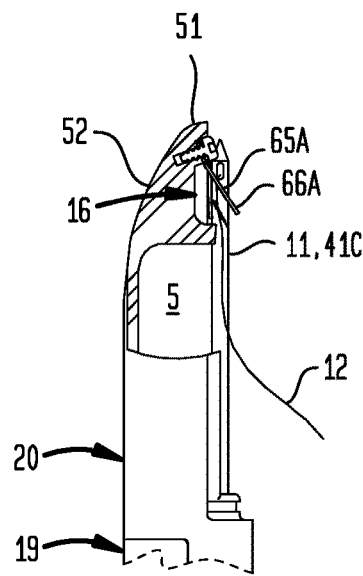
Figure 24B:
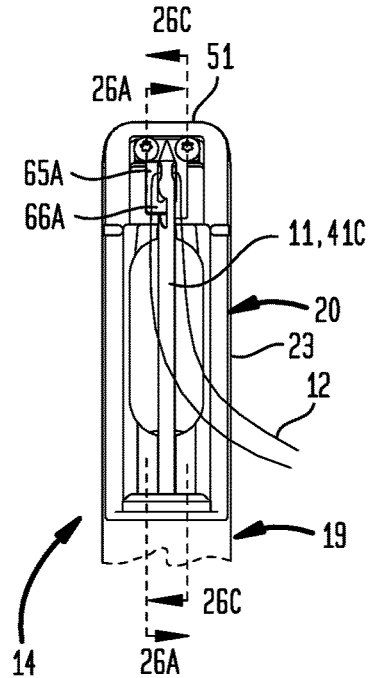

FIG. 22A is the cross section view 24A-24A shown in FIG. 24B depicting the unidirectional movement of the thread carrier in response to operation of the ratchet assembly to a thread carrier second position in which the thread carrier passes through the substrate capture chamber into the thread capture chamber and prohibited from being retracted back to the thread carrier first position within the handle of the suture apparatus.

Figure 22B:
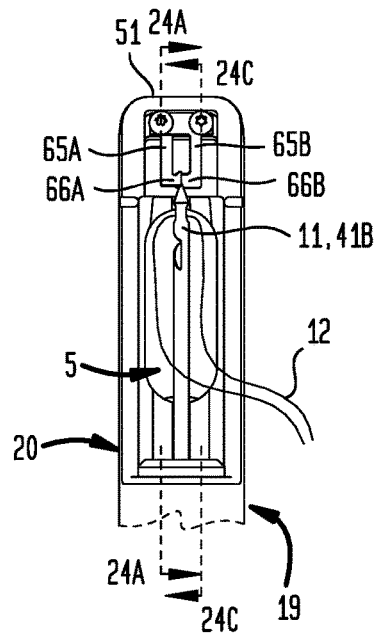

FIG. 22B is a top plan view of the suturing probe having the top portion removed to depict the unidirectional movement of the thread carrier in response to operation of the ratchet assembly to a thread carrier second position in which the thread carrier passes through the substrate capture chamber into the thread capture chamber and prohibited from being retracted back to the thread carrier first position within the handle of the suture apparatus.

Figure 22C:
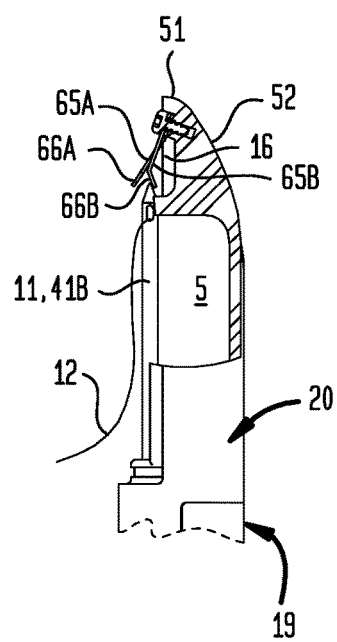

FIG. 22C is the cross section view 24C-24C shown in FIG. 24B depicting the unidirectional movement of the thread carrier in response to operation of the ratchet assembly to a thread carrier second position in which the thread carrier passes through the substrate capture chamber into the thread capture chamber and prohibited from being retracted back to the thread carrier first position within the handle of the suture apparatus.

Figure 23A:
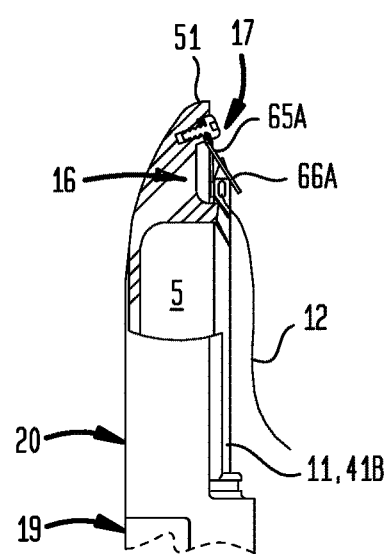
Figure 25A:
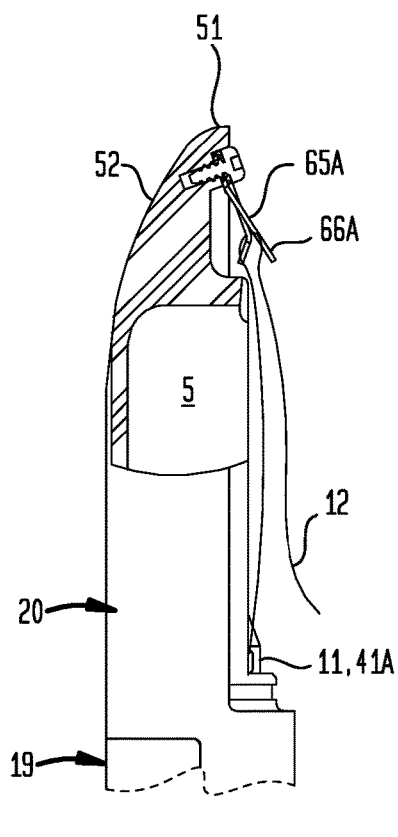
Figure 25B:
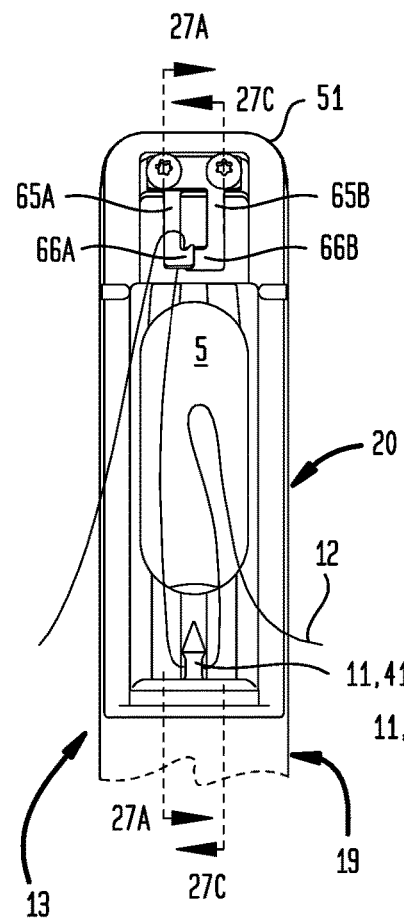

FIG. 23A is the cross section view 25A-25A shown in FIG. 25B depicting the unidirectional movement of the thread carrier in response to operation of the ratchet assembly toward a thread carrier third position in which the thread carrier passes through the substrate capture chamber into the thread capture chamber to engage the thread capture assembly.

Figure 23B:
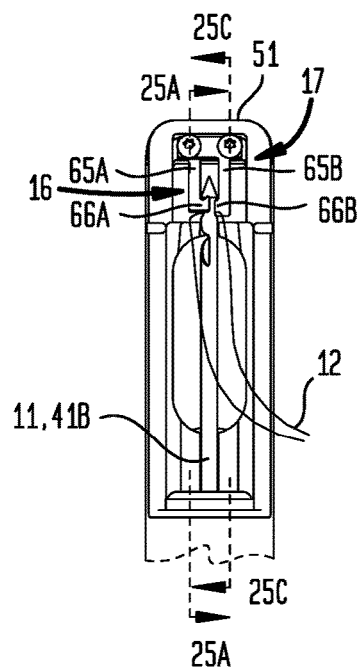

FIG. 23B is a top plan view of the suturing probe having the top portion removed to depict the unidirectional movement of the thread carrier in response to operation of the ratchet assembly toward a thread carrier third position in which the thread carrier passes through the substrate capture chamber into the thread capture chamber to engage the thread capture assembly.

Figure 23C:
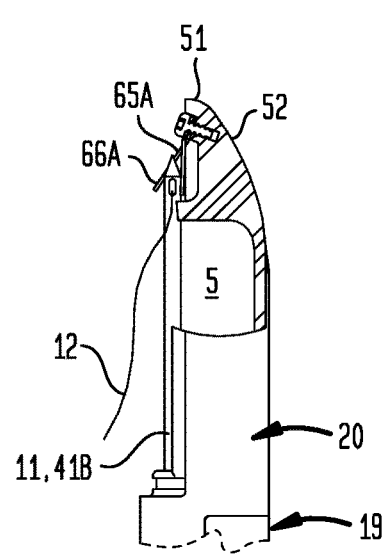

FIG. 23C is the cross section view 25C-25C shown in FIG. 25B depicting the unidirectional movement of the thread carrier in response to operation of the ratchet assembly toward a thread carrier third position in which the thread carrier passes through the substrate capture chamber into the thread capture chamber to engage the thread capture assembly.

FIG. 24A is the cross section view 26A-26A shown in FIG. 26B depicting the unidirectional movement of the thread carrier in response to operation of the ratchet assembly to a thread carrier third position in which the thread carrier passes through the substrate capture chamber into the thread capture chamber to engage the thread capture assembly with a hook aligned in a notch passage.

FIG. 24B is top plan view of the suturing probe having the top portion removed to depict the unidirectional movement of the thread carrier in response to operation of the ratchet assembly to a thread carrier third position in which the thread carrier passes through the substrate capture chamber into the thread capture chamber to engage the thread capture assembly with a hook aligned in a notch passage.

Figure 24C:
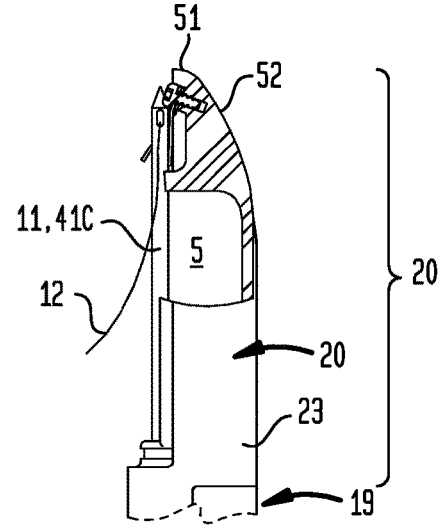

FIG. 24C is the cross section view 26C-26C shown in FIG. 25B depicting the unidirectional movement of the thread carrier in response to operation of the ratchet assembly to a thread carrier third position in which the thread carrier passes through the substrate capture chamber into the thread capture chamber to engage the thread capture assembly with a hook aligned in a notch passage.

FIG. 25A is the cross section view 27A-27A shown in FIG. 27B depicting the retraction of the thread carrier in response to operation of the ratchet assembly to a thread carrier first position in which the thread carrier disengages the thread capture assembly passing through the substrate capture chamber into the handle forming a thread loop.

FIG. 25B is a top plan view of the suturing probe having the top portion removed to depict the retraction of the thread carrier in response to operation of the ratchet assembly to a thread carrier first position in which the thread carrier disengages the thread capture assembly passing through the substrate capture chamber into the handle forming a thread loop.

Figure 25C:
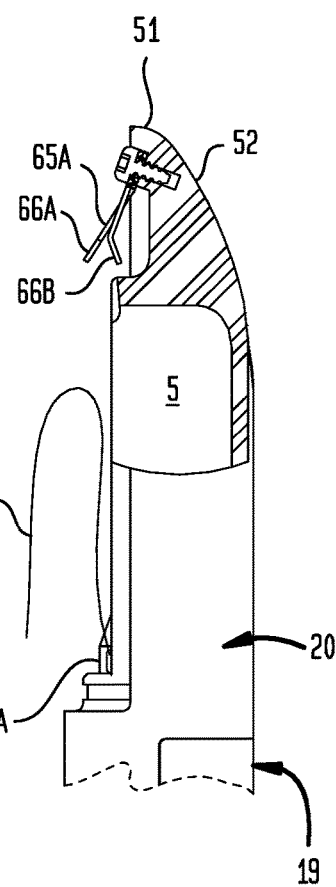

FIG. 25C is the cross section view 27C-27C shown in FIG. 27 depicting the retraction of the thread carrier in response to operation of the ratchet assembly to a thread carrier first position in which the thread carrier disengages the thread capture assembly passing through the substrate capture chamber into the handle forming a thread loop.

Figure 26:
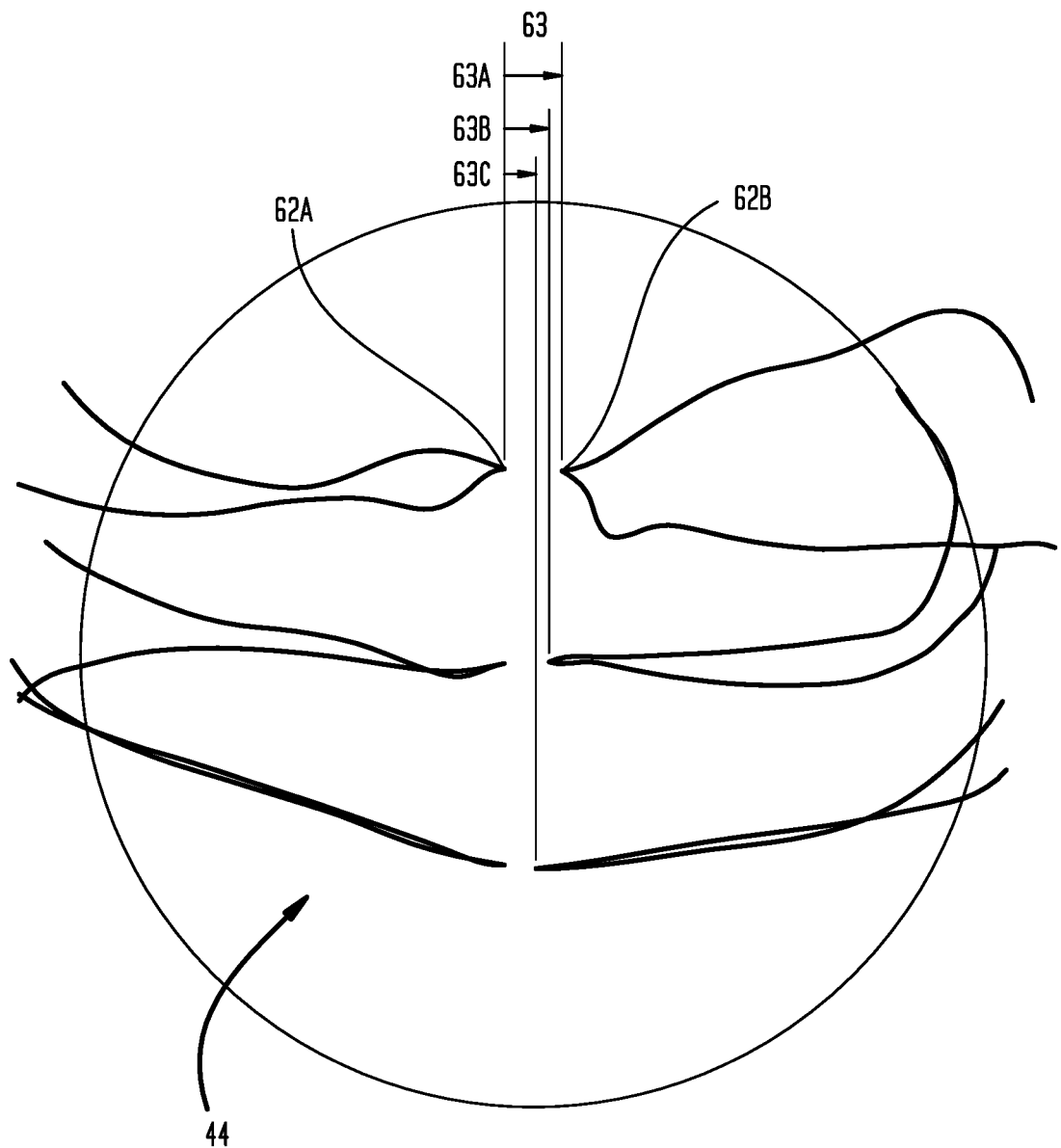

FIG. 26 is an illustration which compares the suture purchase of the inventive suturing apparatus of the particular embodiment shown in FIGS. 1 through 27 with conventional suturing apparatus.

IV. DETAILED DESCRIPTION OF THE PREFERRED EMBODIMENTS

Generally referring to FIGS. 1 through 26, embodiments of a suturing apparatus (1) including one or more of: a housing (2) which maintains in operable relation a valved conduit (3) operable to regulate fluid flow (4) between a substrate capture chamber (5) and a vacuum port (6) or an ambient pressure port (7) to regulate pressure (8) within the substrate capture chamber (5) in relation to the ambient pressure (9) surrounding the substrate capture chamber (5) and a thread carrier driver (10) disposed to axially move a thread carrier (11) carrying a thread (12) between a retracted condition (13) disposing the thread carrier (11) outside of the substrate capture chamber (5) and an extended condition (14) in which a thread carrier terminal end (15) of the thread carrier (11) passes axially through the substrate capture chamber (5) into a thread capture chamber (16) to engage a thread capture assembly (17) which captures the thread (12) to generate a thread loop upon return of the thread carrier (11) toward the retracted condition (13).

Now referring primarily to FIGS. 1 through 12, embodiments of the housing (2) can include a handle (18) and a tubular member (19) which outwardly axially extends from the handle (18) terminating in a suturing probe (20). The handle external surface (21) can, but need not necessarily, be configured to be grippingly engaged by the human hand. The tubular member external surface (22) and the suturing probe external surface (23) can, but need not necessarily, be configured to pass through small incisions or natural body openings to engage the deep surface of the skin, fascia, fat, or muscle of a patient. Accordingly, the handle (18), the tubular member (19), and the suturing probe (20) can be scaled depending upon the application.

Figure 1:
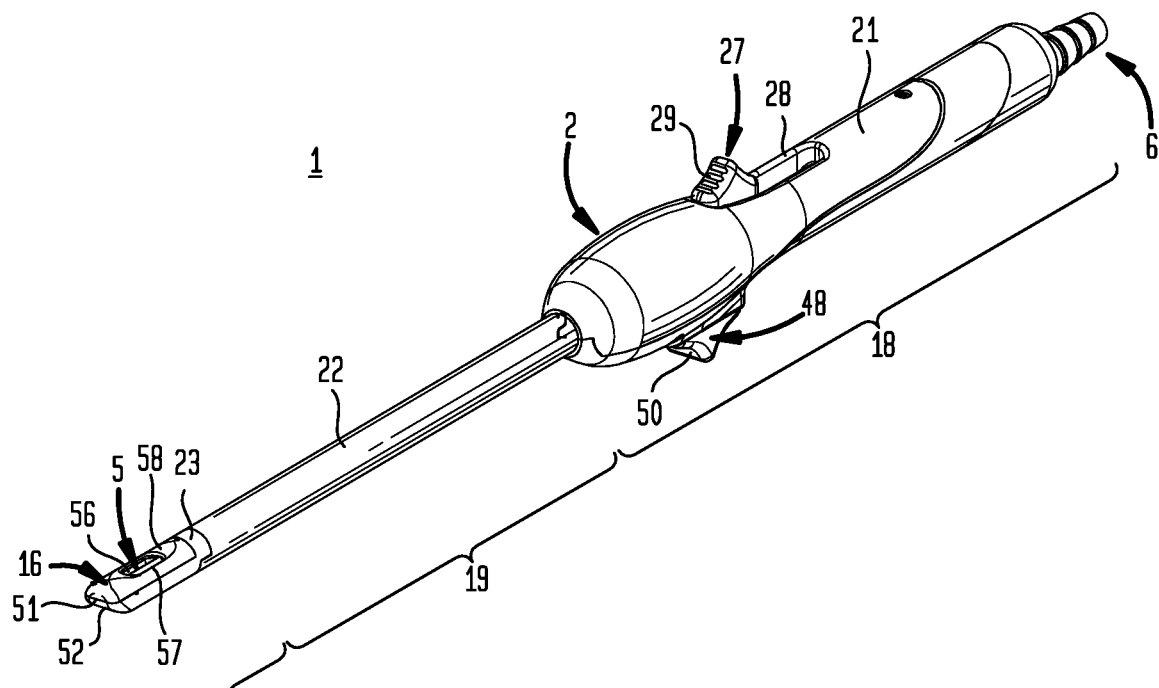
FIG. 1 is a first perspective view of a particular embodiment of a suturing apparatus.
Figure 2:
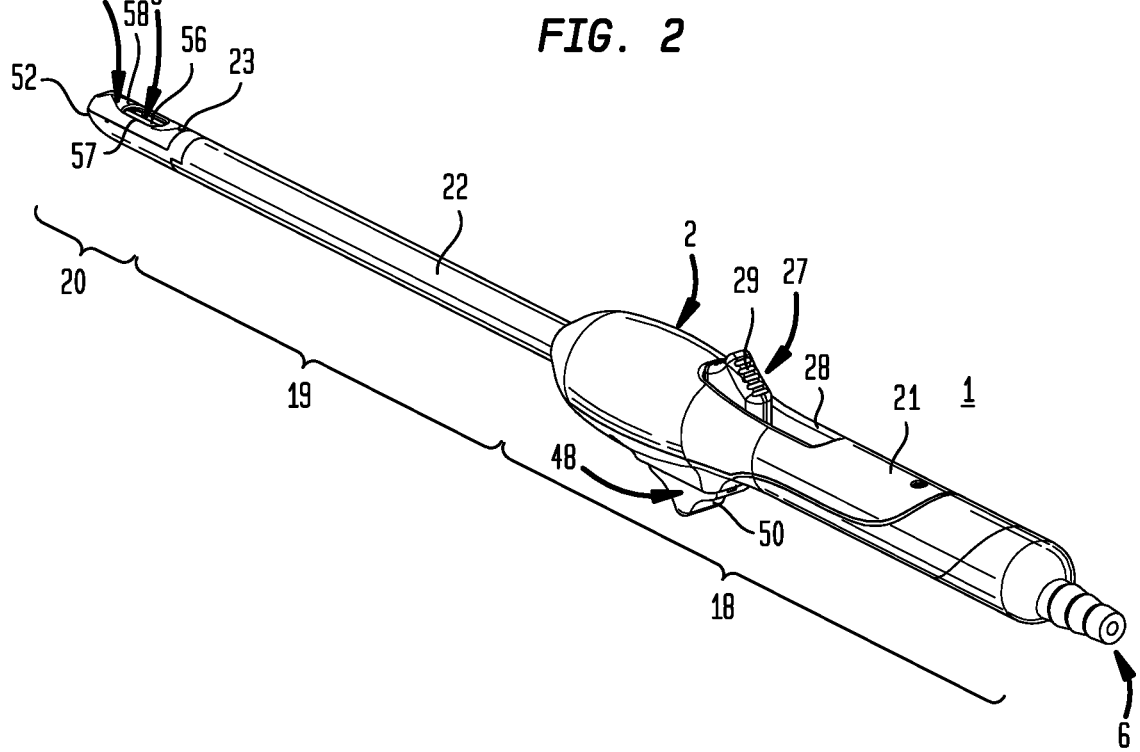
FIG. 2 is a second perspective view of a particular embodiment of the suturing apparatus.
Figure 3:
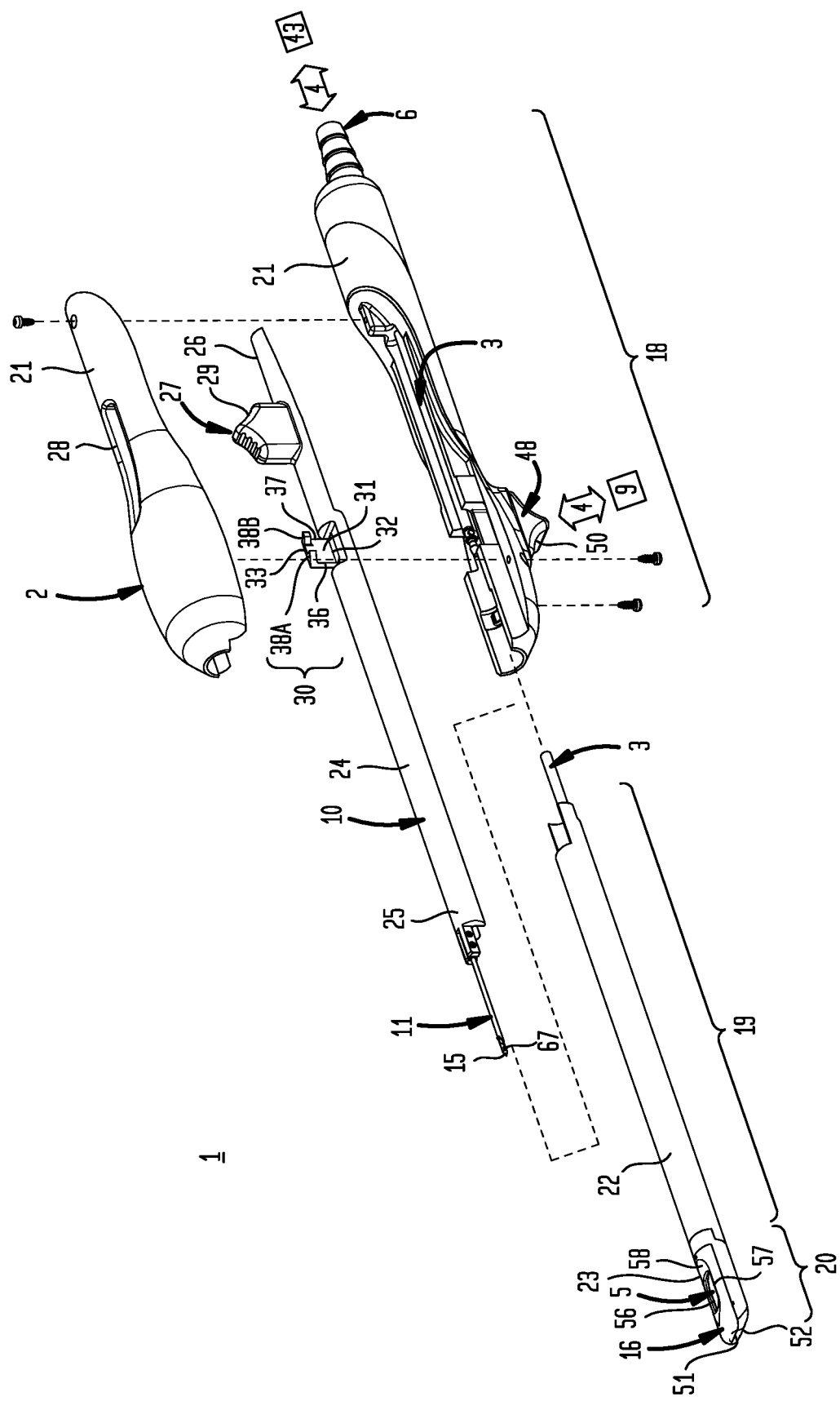
FIG. 3 is an exploded view of a particular embodiment of the handle of the suturing apparatus shown in FIGS. 1 and 2.

Now referring primarily to FIG. 3, the housing (2) can receive in axial sliding engagement a thread carrier driver (10). The thread carrier driver (10) comprises an elongate drive member (24) having a length disposed between a drive member first end (25) and a drive member second end (26). The elongate drive member (24) moves axially inside of the handle (18) in response to a drive member actuator (27). As to particular embodiments, a drive member actuator slot (28) can be disposed in the housing (2) and the drive member actuator (27) can be configured to extend through the drive member actuator slot (28) to present a pressible drive member actuator button (29) which upon forcible urging generates corresponding axial movement of the elongate drive member (24) inside of the handle (18).

Figure 6:
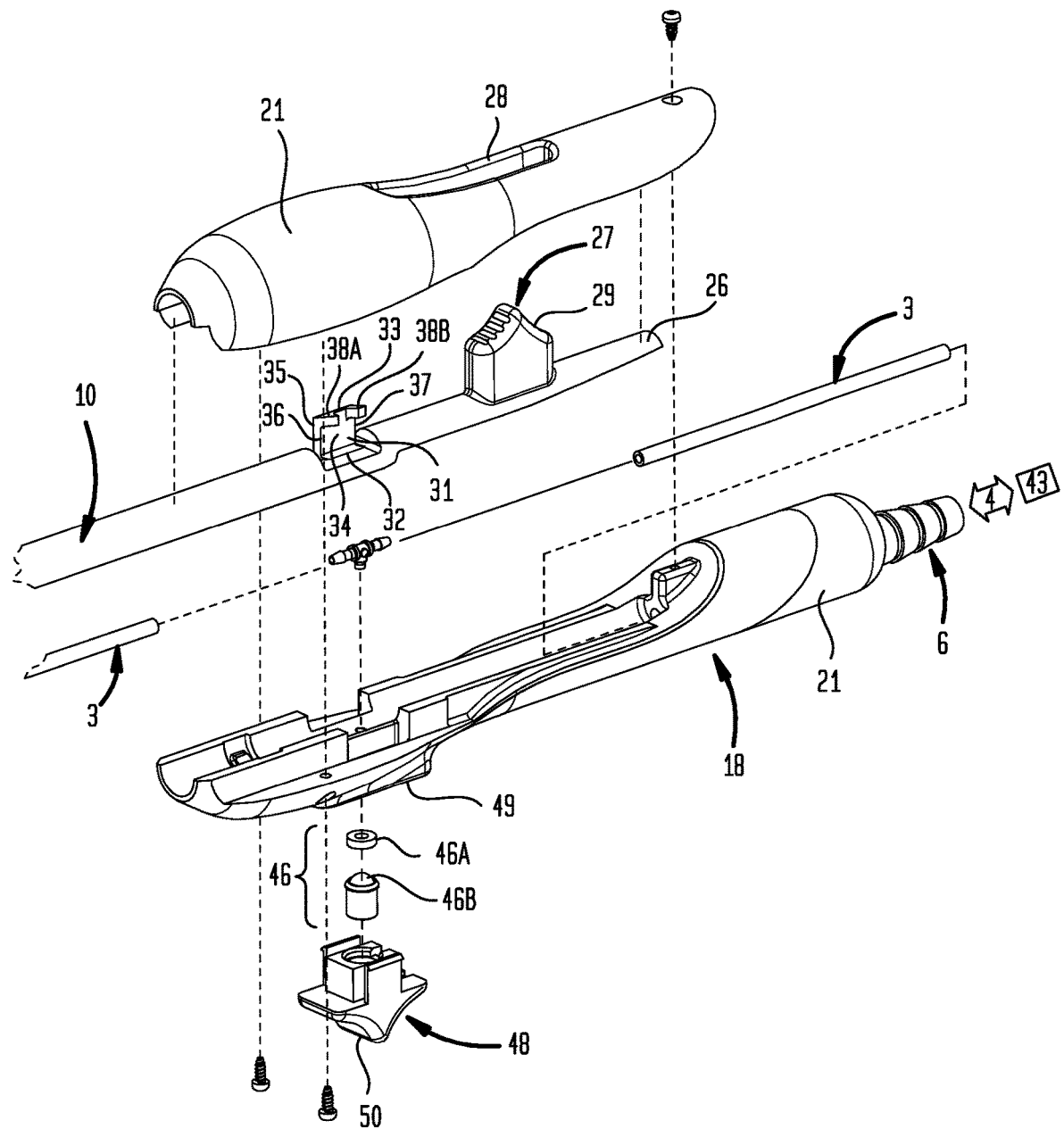
FIG. 6 is an exploded view of a particular embodiment of the valve actuator of the suturing apparatus shown in FIGS. 1 and 2.
Figure 7:
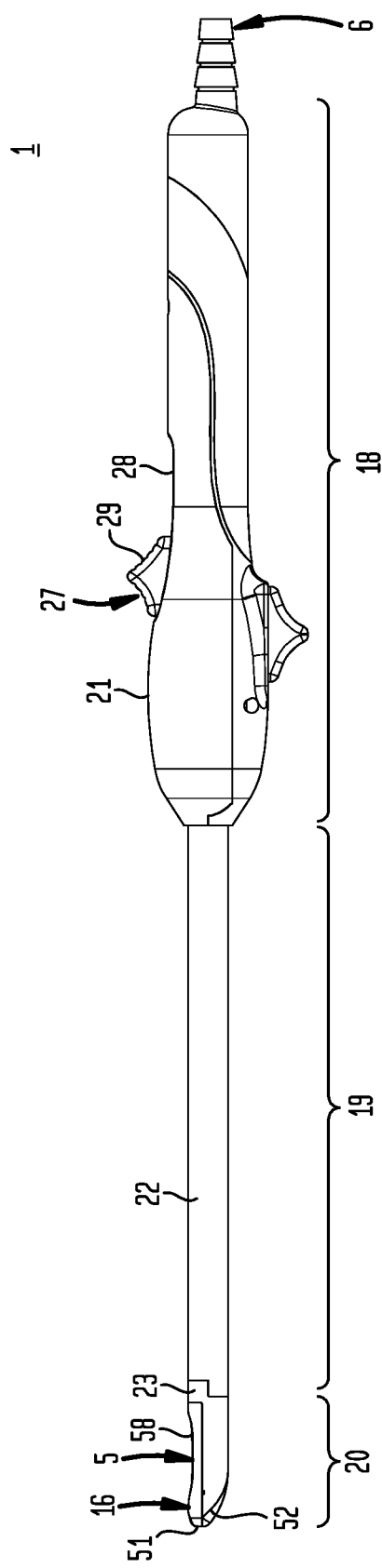
FIG. 7 is a first side elevation view of a particular embodiment of the suturing apparatus.
Figure 8:
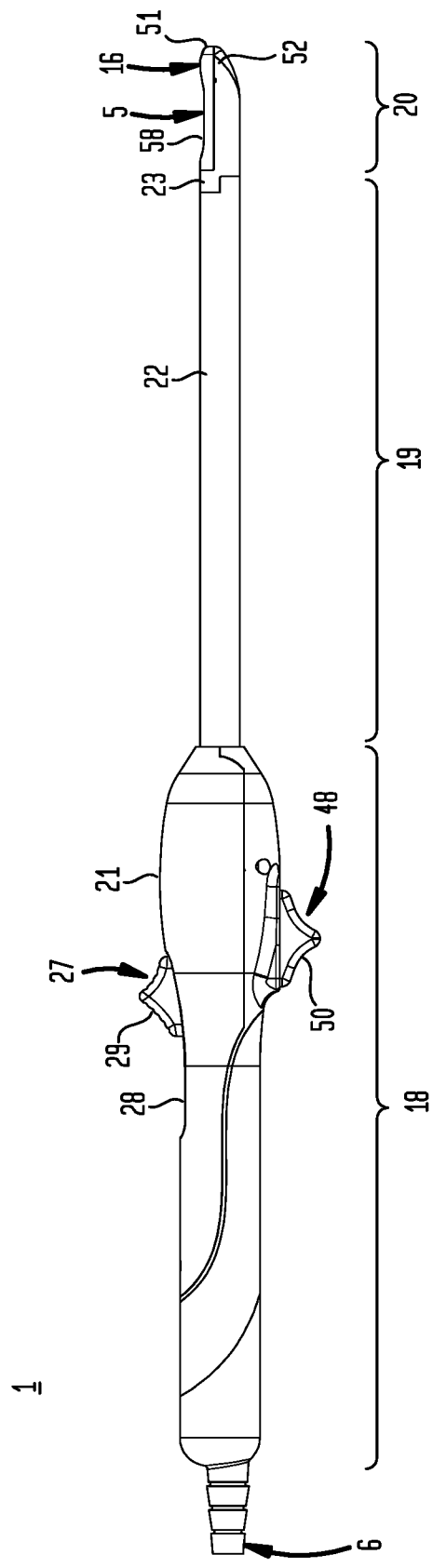
FIG. 8 is a second side elevation view of a particular embodiment of the suturing apparatus.
Figure 11:
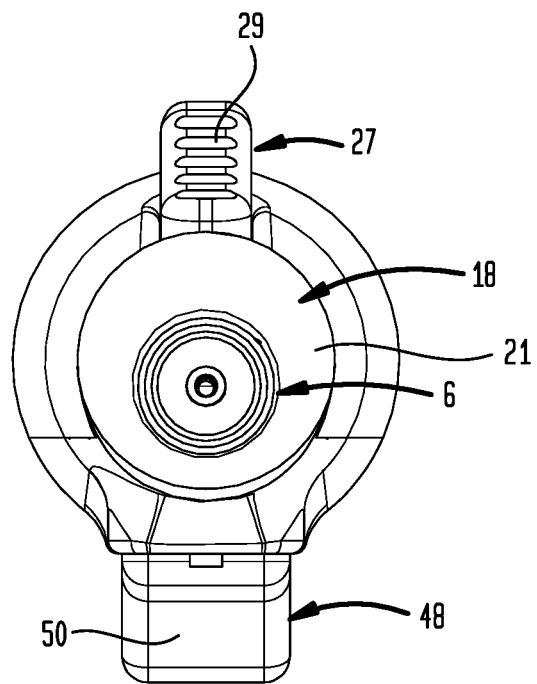
FIG. 11 is a first end view of a particular embodiment of the suturing apparatus.
Figure 12:
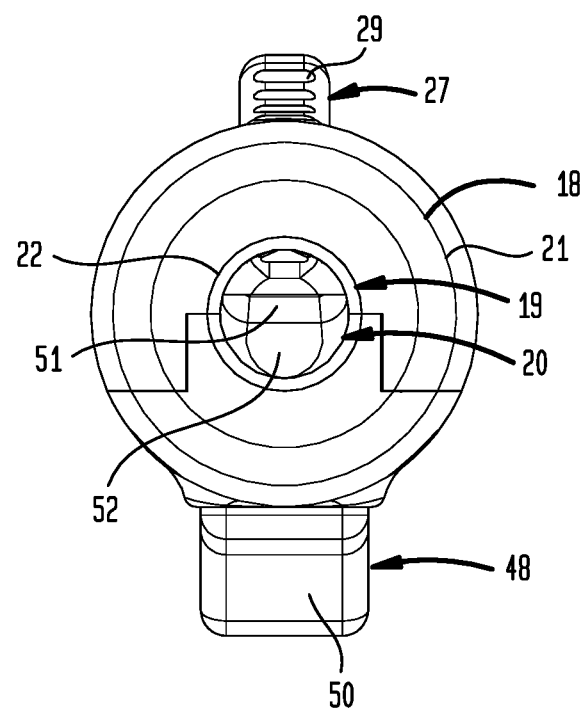
FIG. 12 is as second end view of a particular embodiment of the suturing apparatus.

Now referring primarily to FIGS. 3, 6, 13A, 13B and 13D, and 14B and 14D, particular embodiments of the thread carrier driver (10) can further include a ratchet assembly (30). The ratchet assembly (30) can comprise a resiliently flexible ratchet member (31) having a length disposed between a member first end (32) coupled to the elongate drive member (24) and extending outwardly to terminate in a member second end (33). The resiliently flexible ratchet member (31) can have a first face (34) opposite a second face (35) joined at the periphery by a leading edge (36) opposite a trailing edge (37). At least one angled tooth (38) can outwardly extend from the first face (34) proximate the member second end (33). As to particular embodiments, as shown in the examples of FIGS. 3 and 6, a pair of angled teeth (38A) (38B) can outwardly extend from the first face (34) proximate the member second end (33). A peg (39) having a fixed location on the housing internal surface (40) extends outwardly to engage the flexible member second end (33).

Figure 14A:
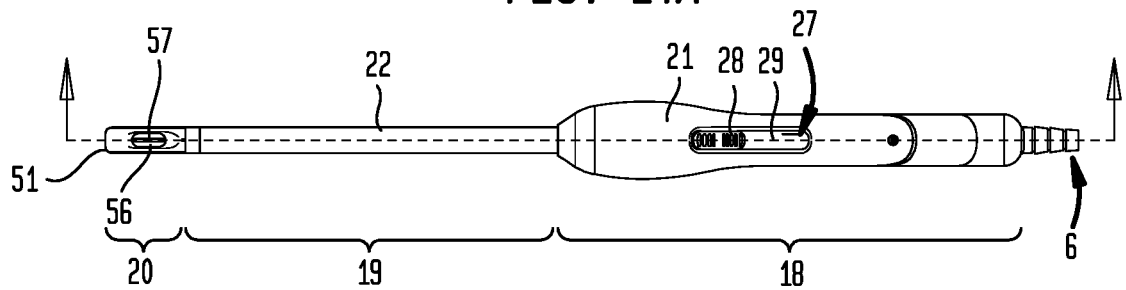
FIG. 14A is a top plan view of a particular embodiment of the suturing apparatus depicting the location of cross section 14A-14A.
Figure 14B:
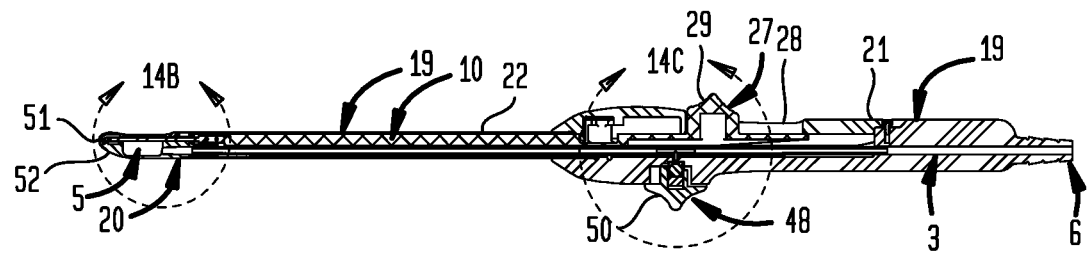
FIG. 14B is a cross section view 14A-14A as shown in FIG. 14.
Figure 14C:
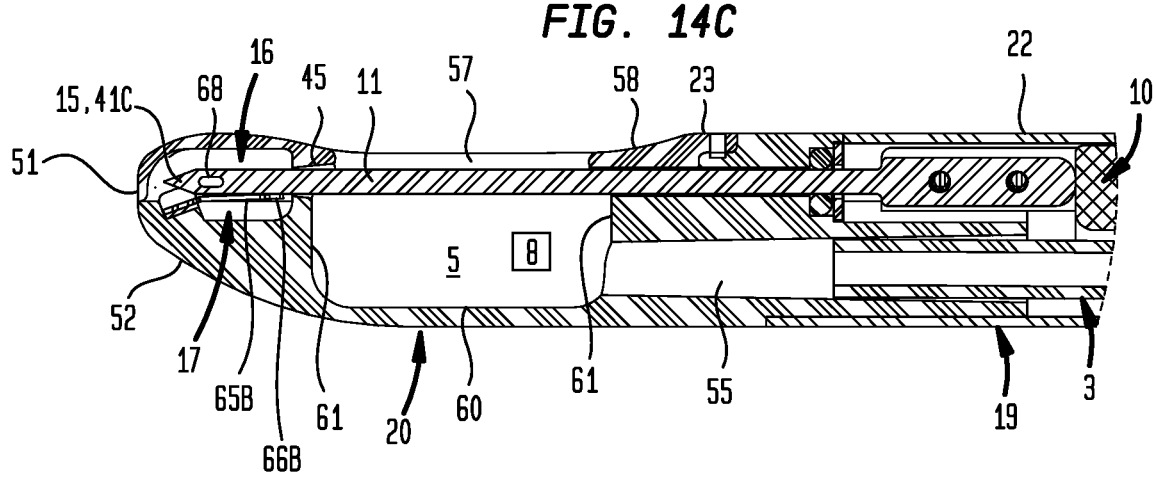
FIG. 14C is an enlarged view of portion 14B shown in FIG. 14A which depicts the thread carrier in a third thread carrier position extended to pass through the substrate capture chamber into the thread capture chamber to engage a thread capture assembly.
Figure 14D:
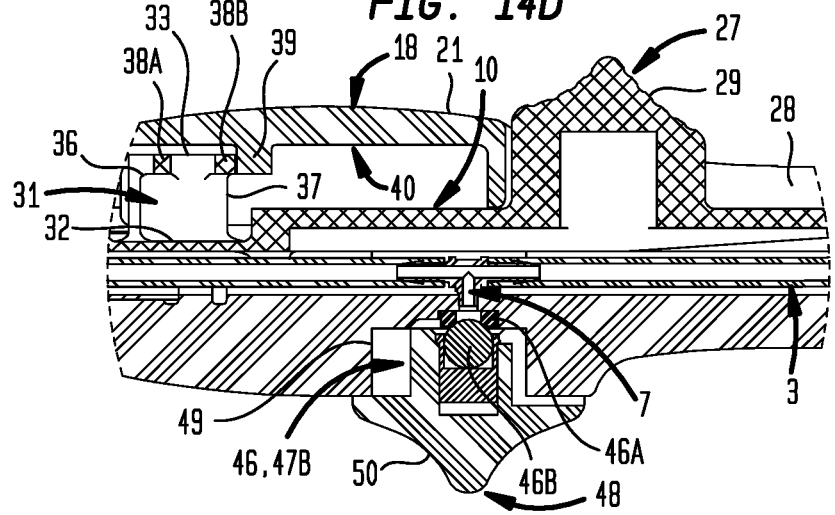
FIG. 14D is an enlarged view of portion 14C shown in FIG. 14A having the ambient pressure port in the closed condition.
Figure 15A:
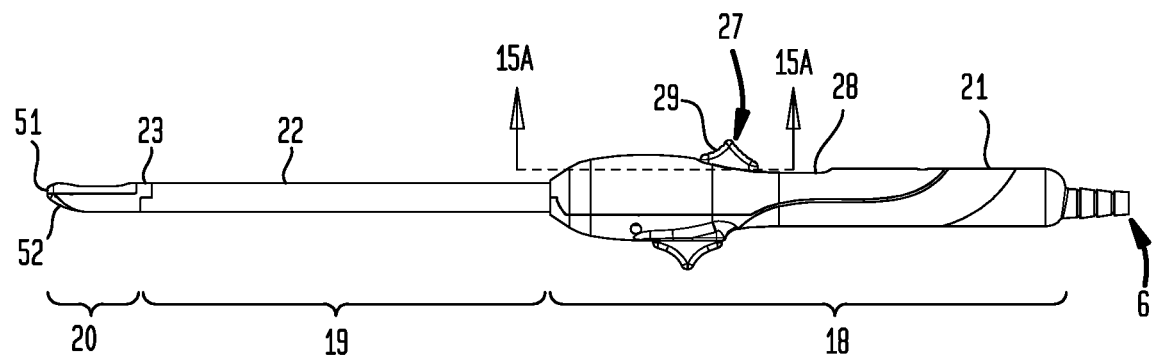
FIG. 15A is a first side elevation view of a particular embodiment of the suturing apparatus depicting the location of cross section 15A-15A.
Figure 15B:
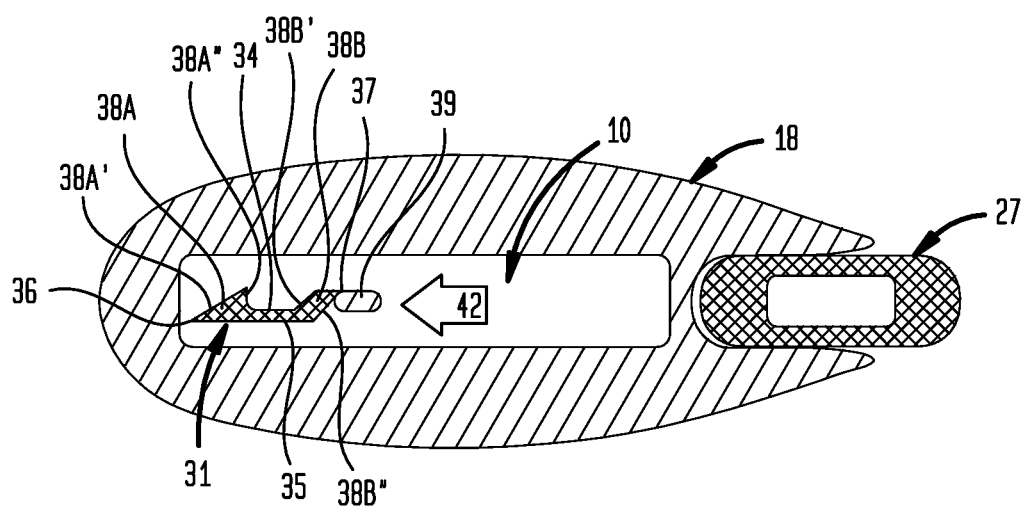
FIG. 15B is a cross section view 15A-15A as shown in FIG. 15.

Now referring primarily to FIGS. 13D and 14D, the thread carrier driver (10) can be slidably axially moved in the housing (2) to concurrently axially move the thread carrier (11) and the resiliently flexible ratchet member (31). The peg (39) can have a location proximate the leading edge (36) of the resiliently flexible ratchet member (31) (as shown in the example of FIG. 13D) to dispose the thread carrier terminal end (15) at a thread carrier first position (41A) outside of the substrate capture chamber (5). The resiliently flexible ratchet member (31) flexes in a first direction (42A) to allow at least one angled tooth (38) or the first of a pair of angled teeth (38A) (or the first of a plurality of angled teeth) to unidirectionally slidably engage the peg (39) over the first tooth angled face (38A') to dispose the peg (39) adjacent the corresponding first tooth base (38A") or between the pair of angled teeth (38A) (38B) adjacent the first tooth base (38A") and to concurrently dispose the thread carrier terminal end (15) at a thread carrier second position (41B) inside of the substrate capture chamber (5). Once the peg (39) traverses the first tooth angled face (38A') of at least one angled tooth (38) toward the trailing edge (37) of the resiliently flexible ratchet member (31), the resiliently flexible ratchet member (31) returns toward the unflexed position to dispose the peg (39) adjacent the first tooth base (38A'), which prohibits the peg (39) from traveling toward the leading edge (36) of the resiliently flexible ratchet member (31).

Now referring primarily to FIG. 14D, the peg (39) can be disposed between a pair of angled teeth (38A) (38B) adjacent the first tooth base (38A') of the first of the pair of angled teeth (38A). The resiliently flexible ratchet member (31) again flexes in the first direction (42A) to allow a second of the pair of teeth (38B) to unidirectionally slidably engage the peg (39) with the second tooth angled face (38B') to dispose the peg (39) adjacent the second tooth base (38B") of the second of the pair of angled teeth (38B) and to concurrently dispose the thread carrier terminal end (15) at a third thread carrier position (41C) in the thread capture chamber (16). The second tooth base (38B") (or the tooth proximate the trailing edge (37) of the resiliently flexible ratchet member (31)) can be angled to flex the resiliently flexible member (31) in a second direction (42B) to allow the member second face (33) to unidirectionally slidably engage the peg (39) to position the peg (29) a distance away from the leading edge (36) of the resiliently flexible ratchet member (31) and concurrently dispose the thread carrier terminal end (15) at the thread carrier first position (41A) at a location outside of the substrate capture chamber (5).

Now referring primarily to FIGS. 3, 6, 13B, 13C, and 13D, the housing (2) can be configured to provide a vacuum port (6) opening on the handle external surface (21) (as shown in the example of FIGS. 3 and 6). The vacuum port (6) can be coupled to a vacuum source (43) (as shown in the example of FIGS. 3 and 6). The vacuum source (43) can comprise any of a variety of conventional vacuum or suction pumps. The valved conduit (3) can be connected between the vacuum port (6) and the substrate capture chamber (5) (as shown in the examples of FIGS. 3, 13B and 13C). The vacuum source (43) can be operated to generate a reduced chamber pressure (8) in the substrate capture chamber (5). As to particular embodiments, the reduced chamber pressure (8) can be sufficient to draw a fold of a substrate (44) or a pair of layers of the substrate (44), or a plurality of layers of the substrate (44) into the substrate capture chamber (5). The housing (2) can be further configured to provide an ambient pressure port (7) opening on the handle external surface (21) to ambient pressure (9). The valved conduit (3) can be operated to regulate fluid flow (4) between the vacuum port (6) and the substrate capture chamber (5) or the ambient pressure port (7) to regulate chamber pressure (8) within the substrate capture chamber (5) in relation to the ambient pressure (9) surrounding said substrate capture chamber (5). The valved conduit (3) can include a valve (46) operable between an ambient pressure port closed condition (47B) in which fluid flow (4) occurs primarily between the substrate capture chamber (5) and the vacuum source (43) to generate reduced chamber pressure (8) in the substrate capture chamber (5) and an ambient pressure port open condition (46A) in which fluid flow occurs primarily between the ambient pressure port (7) and the vacuum source (43) generating ambient pressure (9) in the substrate capture chamber (5). As reduced chamber pressure (8) in the substrate capture chamber (5) approaches ambient pressure (9) the substrate (44) captured inside of the substrate capture chamber (5) can be released to a location outside of the substrate capture chamber (5).

Now referring primarily to FIGS. 6 and 13D and 14D, as to particular embodiments, the valve (46) can, but need not necessarily, include a valve seat (46A) surrounding the ambient pressure port (7) and a valve ball (46B) which can be positioned on the valve seat (46A) to generate the ambient pressure port closed condition (47B) (as shown in the example of 14D). The valve ball (46B) can be moved in relation to the valve seat (46A) to generate the ambient port open condition (47A) (as shown in the example of FIG. 13D). As to particular embodiments, the valved conduit (3) can further include a valve actuator (48) coupled to the valve (46). The valve actuator (48) can be moved to correspondingly position the valve ball (46B) between the ambient pressure port open position (47A) and the ambient pressure port closed condition (47B). As to particular embodiments, a valve actuator slot (49) can be disposed in the housing (2) and the valve actuator (48) can be configured to extend through the valve actuator slot (49) to present a pressible valve actuator button (50) of the valve member actuator (46) which upon forcible urging generates corresponding movement of the valve ball (46B) in relation to the valve seat (46A) to correspondingly provide the ambient pressure port open condition (47A) and the ambient pressure port closed condition (47B).

Now referring primarily to FIGS. 13A, 13B, 13C, 17A and 17B, embodiments of the suturing apparatus (1) further include a suturing probe (20) outward axially extending from the tubular member (19) to terminate in a probe tip (51). The suturing probe external surface (23) can, but need not necessarily, be configured as an extension of the external dimensions of the tubular member (29) allowing the probe tip (51) to pass through small incisions or natural body openings to engage the deep surface of the skin, fascia, fat, or muscle of a patient. As to particular embodiments, the suturing probe (20) can have a generally cylindrical suturing probe external surface (23) terminating in a hebetated probe tip (51). As to particular embodiments, the suturing probe external surface (23) can include a tapered, beveled, or sloped surface approaching the probe tip (51) to reduce dimensions at the probe tip (51). As to the particular embodiment shown in the example of FIG. 17B, the suturing probe external surface (23) can take the general form of a truncated cylinder in which a plane inclined in relation to the cylindrical axis of the suturing probe (20) generally defines an inclined probe face (52) terminating at the probe tip (51). There can be an advantage in an inclined probe face (52) as it allows the suturing probe (20) additional ingress in tissues with a lesser amount of tissue dissection or trauma.

Again, referring to FIGS. 13A, 13B, 13C, 17A and 17B, embodiments of the suturing probe (20) include a suturing probe internal surface (53) which can, but need not necessarily be, partitioned into an enclosed thread capture chamber (16) containing a thread capture assembly (17) adjacent a substrate capture chamber (5). The substrate capture chamber (5) can be connected to two longitudinal channels (54) (55). The thread carrier (11) reciprocally travels in the first longitudinal channel (54) in response to movement of the thread carrier driver (10). The second longitudinal channel (55) couples the substrate capture chamber (5) to the valved conduit (3) through which fluid flow (4) passes to regulate the chamber pressure (8) within the substrate capture chamber (5). The substrate capture chamber (5) has a chamber opening (56) defined by a chamber port (57) which communicates between the suturing probe internal surface (53) and the suturing probe external surface (23). As to particular embodiments, a recessed peripheral margin (58) can be disposed about the chamber port (57) of the suturing probe external surface (23). The recessed peripheral margin (58) can be configured to lessen the curvature of the suturing probe external surface (23) or to generate a substantially flat peripheral margin (58) about the chamber port (57) (as shown in the example of FIGS. 13B and 13C). The chamber port (57) can be engaged with a substrate (44), and a reduced chamber pressure (8) generated in the substrate capture chamber (5) can dispose or draw folds or layers of the substrate (44) into the substrate capture chamber (5). There can be an advantage in a recessed peripheral margin (58) about the chamber port (57) to increase the area of the suturing probe external surface (23) contacting the substrate (44) under reduced chamber pressure (8) in the substrate capture chamber (5) to decrease movement of the suturing probe (20) in relation to the captured substrate (44).

Figure 20A:
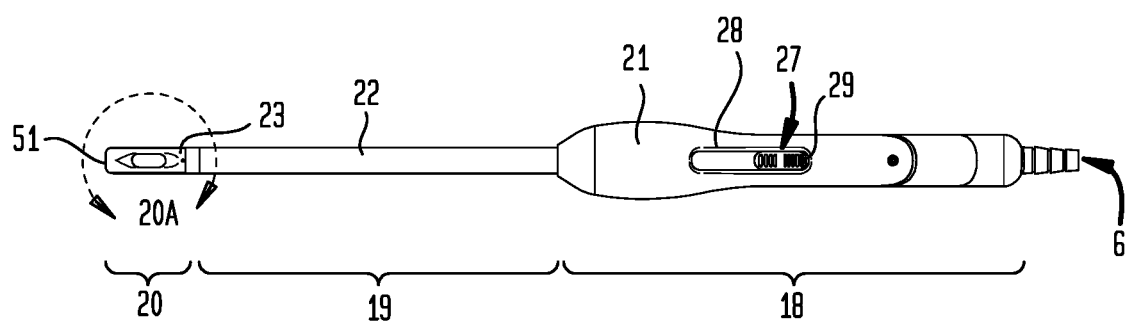
FIG. 20A is a top plan view showing the position of the thread carrier retracted into the handle of the suturing apparatus.
Figure 20B:
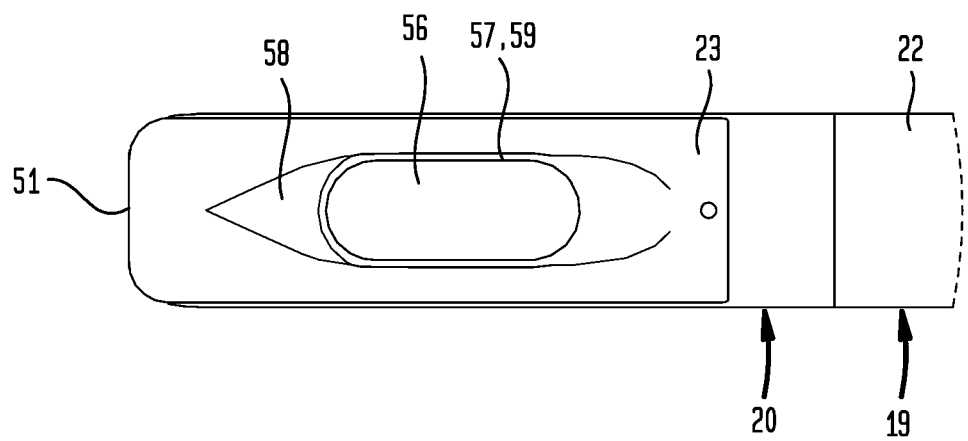
FIG. 20B is an enlarged view of the portion 20A shown in FIG. 20 showing the position of the thread carrier retracted into the handle of the suturing apparatus.

Now referring primarily to FIG. 20B, the chamber port (57) can, but need not necessarily, be disposed in a stadium configuration (59), being a rectangle with semicircles at a pair of opposite sides. Now referring primarily to FIGS. 13C and 17B, the substrate capture chamber (5) can, but need not necessarily, have a chamber bottom (60) in a stadium configuration disposed opposite the chamber port (57) in stadium configuration connected by a substantially vertical chamber sidewall (61). As to particular embodiments, the vertical chamber side wall (61) can define a periphery of greater circumference than the periphery of the chamber port (57) (also referred to as the "stadium configuration").

Now referring primarily to FIG. 26, there can be an advantage in a substrate capture chamber (5) of stadium configuration (59) in that an increased amount of substrate (44) can be penetrated by the thread carrier (11) to dispose a thread entry point (62A) and a thread withdraw point (62B) a greater distance apart (also referred to as the "suture purchase (63)") as compared to conventional slotted or cylindrical suction chambers. As shown in FIG. 26, the thread purchase (63) generated by use of the inventive substrate capture chamber (5) having a stadium configuration (59) (shown as suture purchase (63A)) is substantially greater than that obtained using a suction chamber of cylindrical configuration (suture purchase (63B)) or obtained using a conventional suction chamber of slotted configuration (thread purchase (63C)). It may be that the conventional cylindrical configuration draws the substrate into a conical configuration within the conventional cylindrical suction chamber and the conventional needle only penetrates the substrate proximate the apex of the cone. It may be that the conventional slotted suction chamber does not have sufficient volume to dispose the substrate a sufficient distance into the conventional slotted chamber and the conventional needle only penetrates the substrate layers in adjacent relation close to the fold or edges.

Now referring primarily to FIGS. 13C, 14C, 17B, and 18B, embodiments of the suturing probe internal surface (53) can define a thread capture chamber internal surface (64) defining the thread capture chamber (16). A thread carrier channel (45) communicating between the thread capture chamber (16) and the substrate capture chamber (5) allows ingress and egress of the thread carrier terminal end (15) into the thread capture chamber (16) (as shown by the example of FIGS. 13B, 14C, 17B and 18B).

Figure 4:
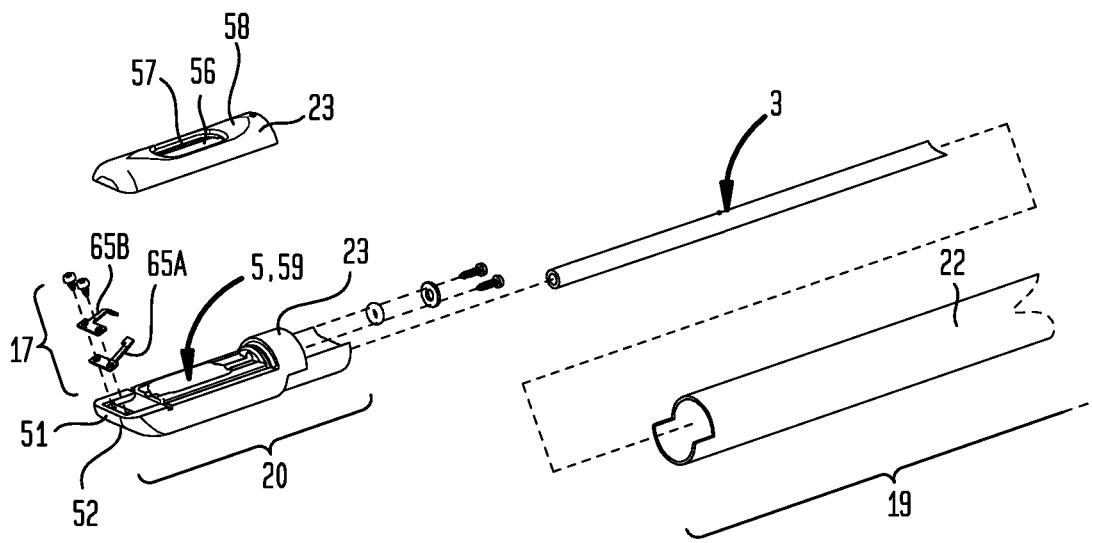
FIG. 4 is and exploded view of a particular embodiment of the suturing probe of the suturing apparatus shown in FIGS. 1 and 2.
Figure 17A:
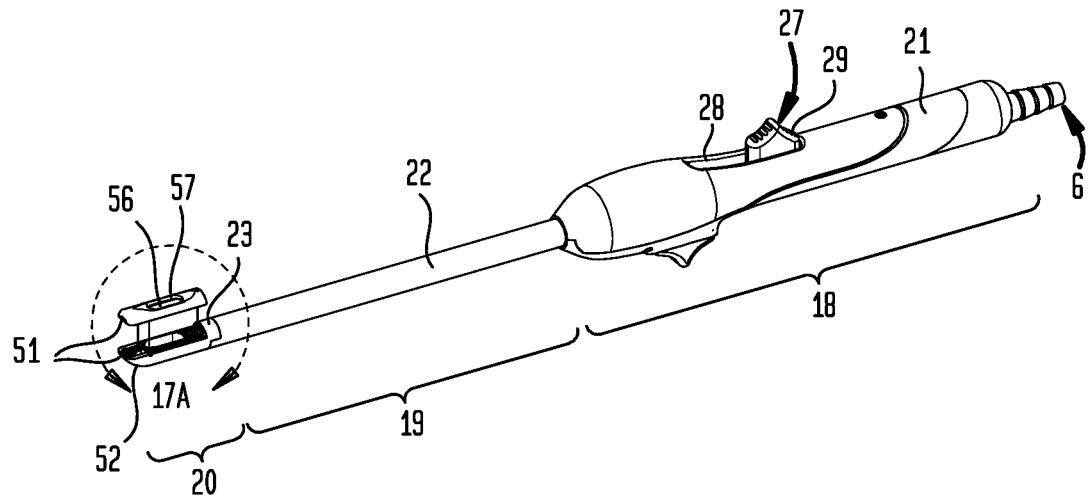
FIG. 17A is a first perspective view a particular embodiment of the suturing apparatus with an exploded view of the suturing probe showing the position of the thread carrier retracted in the handle of the suturing apparatus.
Figure 17B:
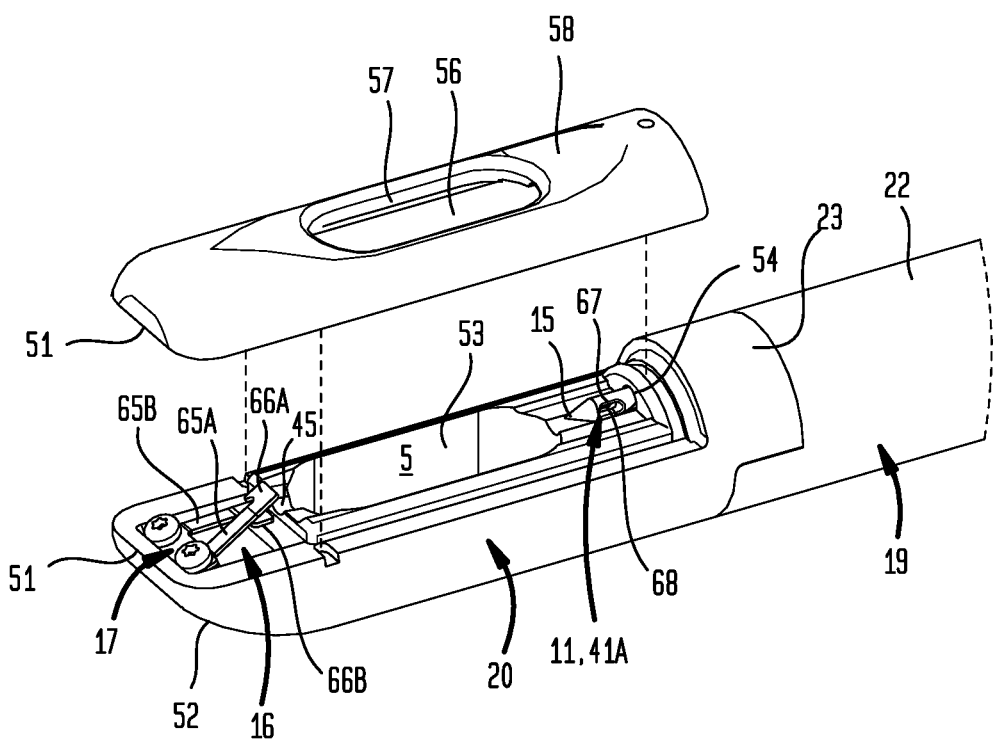
FIG. 17B is an enlarged view of the portion 17A shown in FIG. 17 showing the position of the thread carrier retracted in the handle of the suturing apparatus.
Figure 18A:
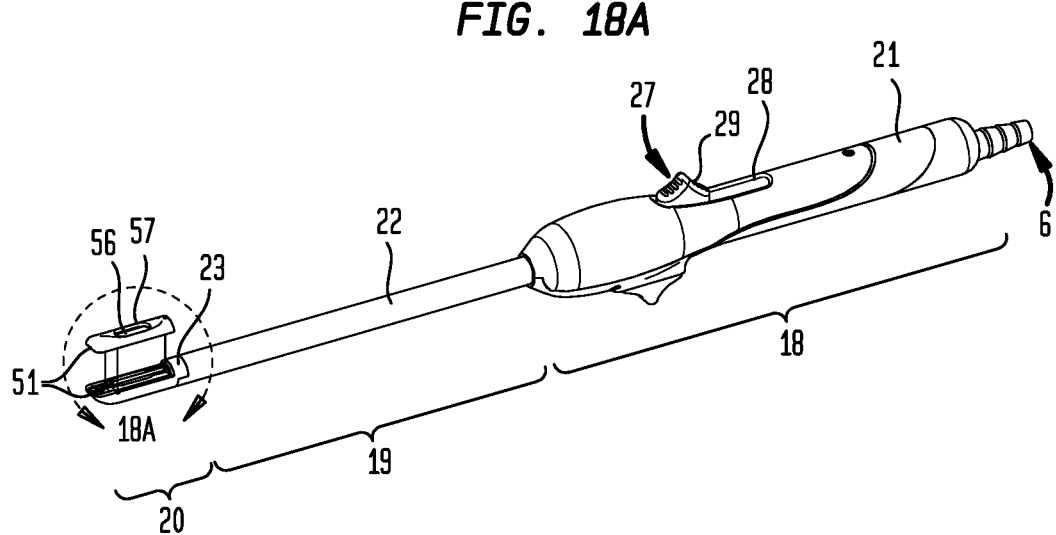
FIG. 18A is a first perspective view a particular embodiment of the suturing apparatus with an exploded view of the suturing probe showing the position of the thread carrier extended into the thread capture chamber and engaged with the thread capture assembly.
Figure 18B:
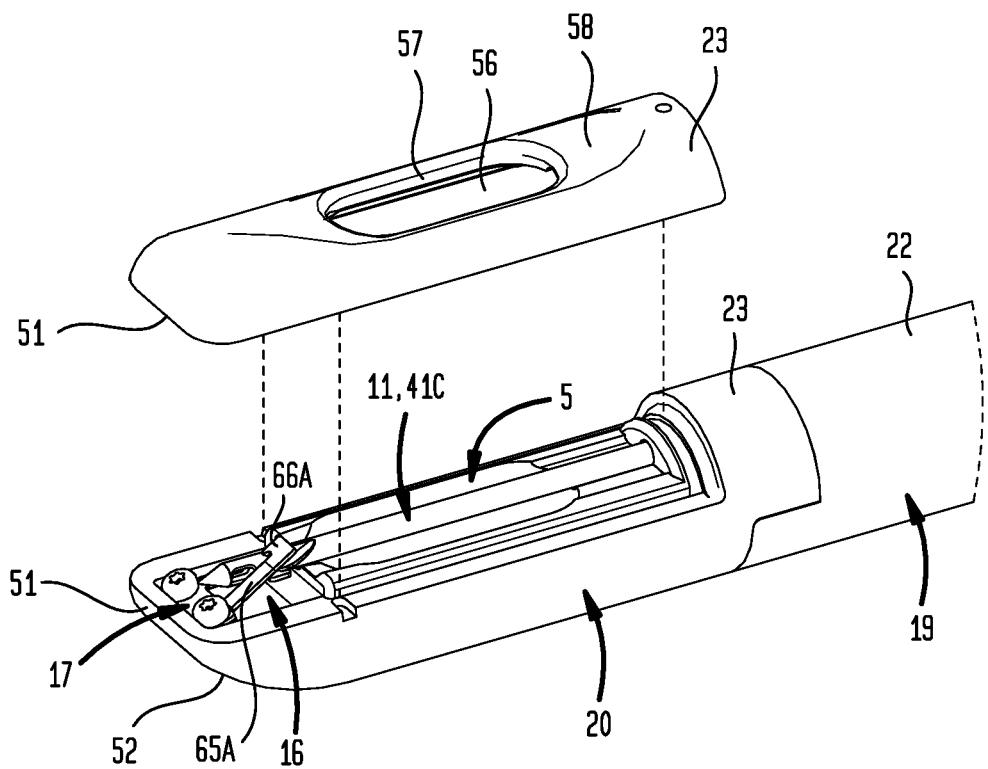
FIG. 18B is an enlarged view of the portion 18A shown in FIG. 18 showing the position of the thread carrier extended into the thread capture chamber and engaged with the thread capture assembly.
Figure 19A:
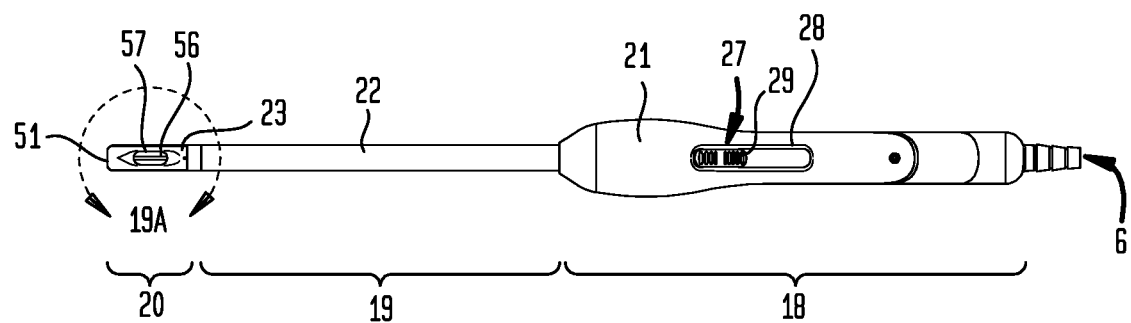
FIG. 19A is a top plan view showing the position of the thread carrier extended into the thread capture chamber and engaged with the thread capture assembly.
Figure 19B:
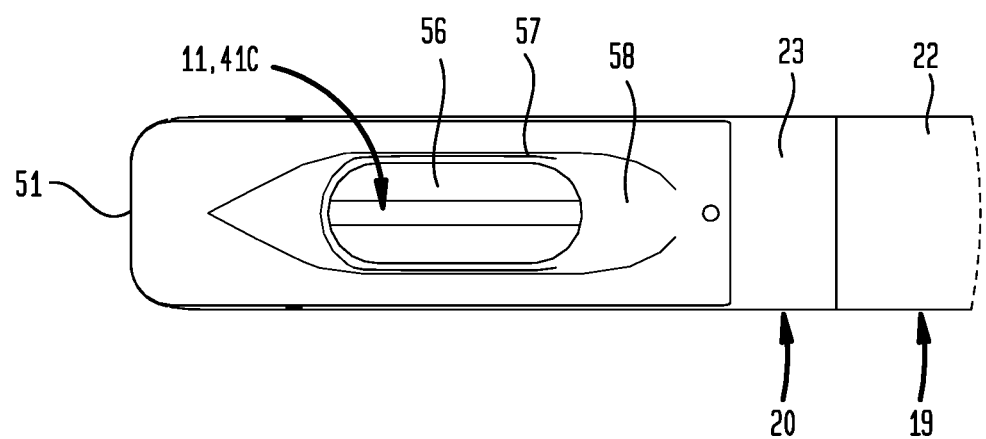
FIG. 19B is an enlarged view of the portion 19A shown in FIG. 19 showing the position of the thread carrier extended into the thread capture chamber and engaged with the thread capture assembly.

Now referring primarily to FIGS. 4 and 17B, a thread capture assembly (17) can be disposed in the thread capture chamber (16). The thread capture assembly (17) can include at least one resiliently flexible hook member (65A) correspondingly terminating in at least one hook (66A). The resiliently flexible hook member (65A) can be coupled to the thread capture chamber internal surface (64) to dispose the hook (66A) at a location to engage the thread carrier (11) and flexing the at least one resiliently flexible hook member (65A). As to particular embodiments, the thread capture assembly (17) can include a pair of resiliently flexible hook members (65A) (65B) each correspondingly terminating in one of a pair of hooks (66A) (66B). The pair of resiliently flexible hook members (65A) (65B) can each be coupled to the thread capture chamber internal surface (64) to dispose the pair of hooks (66A) (66B) a distance apart at locations which allow corresponding engagement on opposed sides of the thread carrier (11), thereby flexing each of the pair of resiliently flexible hook members (65A) (65B) (as shown in the example of FIGS. 14C and 18B). Upon retraction of the thread carrier (11) from the thread capture chamber (16) the pair of resiliently flexible hook members (65A) (65B) each return toward the unflexed condition correspondingly disengaging each of the pair of hooks (66A) (66B) from the thread carrier (11).

Figure 5:
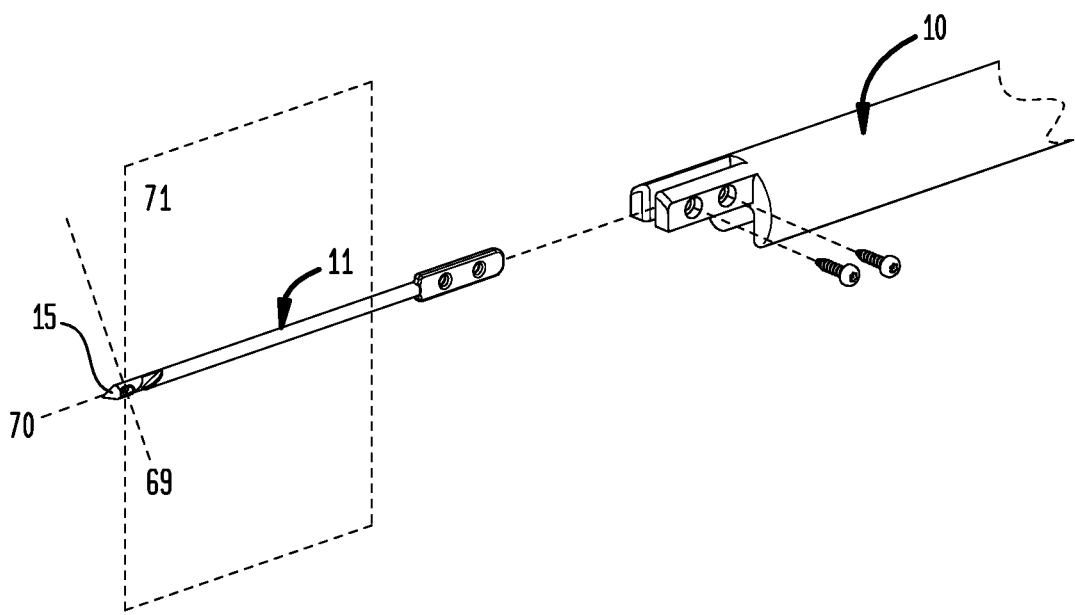
FIG. 5 is an exploded view of a particular embodiment of the thread carrier driver and thread carrier of the suturing apparatus shown in FIGS. 1 and 2.

Now referring primarily to FIGS. 3, 5, and 16, the thread carrier (11) can be coupled to the drive member first end (25) and extend axially outward to terminate in a thread carrier terminal end (15). The thread carrier (11) can comprise a slender rod which can, but need not necessarily, taper approaching the thread carrier terminal end (15). The taper can be sufficient to allow the thread carrier (11) to pass through a particular type of substrate (44), and as to particular embodiments the thread carrier (11) can taper to a sharp point at the thread carrier terminal end (15) to pass through a substrate (44) comprising animal tissue. A thread carrier aperture element (67) can be disposed a distance axially from said thread carrier terminal end (15). The aperture element (67) defines a thread carrier aperture (68). As to particular embodiments, the thread carrier aperture (68) can have a thread carrier aperture axis (69) disposed generally orthogonal to the thread carrier longitudinal axis (70) and generally orthogonal to the plane (71) longitudinally bisecting the chamber port (57) (as shown in the example of FIG. 13C).

Now referring primarily to FIGS. 5 and 16, the thread carrier (11) can further include a notch (72) disposed a distance axially from the thread carrier aperture element (67). The notch (72) defines a notch passage (73) between notch passage first and second ends (73A) (73B) which open on the thread carrier external surface. The notch (73) can be disposed angularly across the thread carrier longitudinal axis (70) of the thread carrier (11) to dispose the notch passage first end (73A) facing away from the chamber port (57) proximal the thread carrier terminal end (15) and the notch passage second end (73B) facing toward the chamber port (57) distal from the thread carrier terminal end (15). The hook (66A) or the pair of hooks (66A) (66B) engage the thread carrier (11) flexing at least one resiliently flexible hook member (65A) or pair of resiliently flexible hook members (65A) (65B) and aligning one of the hooks (66A) with the notch passage second end (73B). Resilient flexure moves the hook (66A) into the notch passage second end (73B). The hook (66A) travels through the notch passage (73) and disengages the thread carrier (11) by egress from the notch passage first end (73A).

Figure 21A:
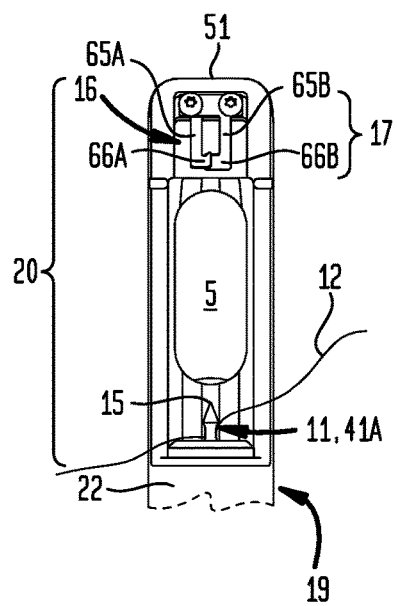
FIG. 21A is a top plan view of the suturing probe having the top portion removed to show the reciprocal movement of the thread carrier in a retracted condition.
Figure 21B:
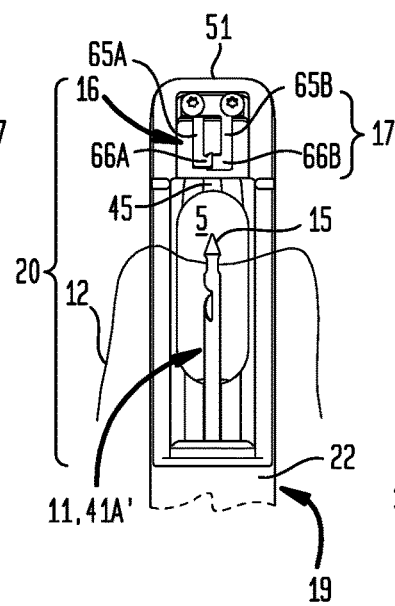
FIG. 21B is a top plan view of the suturing probe having the top portion removed to show the reciprocal movement of the thread carrier in an extended condition passing into the substrate capture chamber.
Figure 21C:
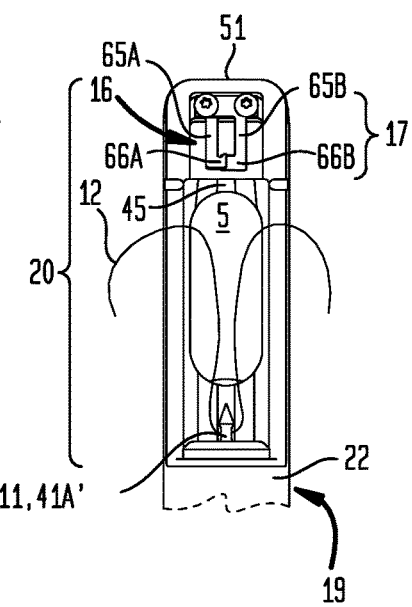
FIG. 21C is a top plan view of the suturing probe having the top portion removed to show the reciprocal movement of the thread carrier returned to the retracted condition outside of the substrate capture chamber.

Now referring primarily to FIGS. 21A through 21C, a thread (12) can be disposed in the thread carrier aperture element (67). As to particular embodiments, the thread carrier driver (10) can be operated bidirectionally to concurrently reciprocally position the thread carrier terminal end (15) between a thread carrier first position (41A) located outside of the substrate capture chamber (5) (as shown by the examples of FIGS. 21A and 21B) and a thread carrier second position (41A') with the thread carrier terminal end (15) located in the substrate capture chamber (5) as shown by (as shown by the example FIGS. 13C and 21C).

Now referring primarily to FIGS. 22A through 22C, as to particular embodiments, the thread carrier driver (10) can be operated to unidirectionally slidably engage a first tooth angled face (38A') of a first one of a pair of angled teeth (38A) (38B) with a peg (39) to dispose the peg (39) between the pair of angled teeth (38A) (38B) adjacent the first tooth base (38A") and to concurrently dispose the thread carrier terminal end (15) at a second position (41B) inside of the thread carrier conduit (45) or the thread capture chamber (16), thereby passing the thread (12) through the substrate (44) captured in the substrate capture chamber (5). Once the peg (39) traverses the first tooth angled face (38A') of the first one of the pair of teeth (38A) (38B), the resiliently flexible ratchet member (31) returns toward the unflexed position to dispose the peg (39) adjacent the first tooth base (38A') which prohibits the peg (39) from traveling toward the leading edge (36) of the resiliently flexible ratchet member (31) and prohibits the thread carrier (11) from being retracted from the thread carrier second position (41B) inside of the thread capture chamber (16).

Now referring primarily to FIGS. 23A through 23C, the thread carrier driver (10) can be operated to unidirectionally slidably engage the peg (39) with the second tooth angled face (38B') of the second one of the pair of teeth (38B) to concurrently engage the thread carrier terminal end (15) with the thread capture assembly (17).

Now referring primarily to FIGS. 14C, 18B, and 24A through 24C, continued operation of the thread carrier driver (10) unidirectionally slidably engages the peg (39) with the second one of the pair of teeth (38B) to dispose the peg (39) adjacent the second tooth base (38B") (as shown in the example of FIG. 14D) and concurrently engage the thread carrier terminal end (15) with the thread capture assembly (17) (as shown FIGS. 14C, 18B, and 24A through 24C) with the hook (66A) aligned with the notch passage second end (73B).

Now referring primarily to FIGS. 25A through 25C, once the peg (39) traverses the second one of the pair of angled teeth (38B) the resiliently flexible ratchet member (31) can return toward the unflexed position to dispose the peg (39) adjacent the second tooth base (38B"). The second tooth base (38B") can be beveled to allow the peg (39) to slidably engage the member second face (35) to travel toward the leading edge (36) of the resiliently flexible ratchet member (31), thereby retracting the thread carrier (11) from the thread capture assembly (17) and withdraw the substrate (44) captured in the substrate capture chamber (5). As the thread carrier (11) retracts, the hook (66A) aligned with the notch passage captures the thread (12) and retains the thread (12) on the hook (66A) (as shown in the example of FIGS. 24B and 25B), thereby disposing the thread (12) between the thread entry point (62A) and the thread withdrawal point (62B) (as shown in the example of FIG. 26).

As can be easily understood from the foregoing, the basic concepts of the present invention may be embodied in a variety of ways. The invention involves numerous and varied embodiments of a mountable carrier and methods for making and using such mountable carrier including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "mount" should be understood to encompass disclosure of the act of "mounting"—whether explicitly discussed or not—and, conversely, were there effectively disclosure of the act of "mounting", such a disclosure should be understood to encompass disclosure of a "mount" and even a "means for mounting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the mountable carriers herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. A thread capture device, comprising:
a thread carrier having:
a terminal end;
a notch disposed in a thread carrier external surface proximate said thread carrier terminal end;
an aperture element passing through and having a pair of openings disposed on opposite sides of said thread carrier, said aperture element disposed separate from and between said thread carrier terminal end and said notch; and
a thread capturer including a first resiliently flexible hook member terminating in a first hook, said thread carrier moves to slidably engage said thread carrier external surface with said first hook, said hook aligning with and passing into a notch passage first end and out of a notch passage second end each open on said thread carrier external surface.

2. The device of claim 1, wherein said notch defines a notch passage having a notch passage first end and a notch passage second end, wherein each of said notch passage first and second ends open on said thread carrier external surface.

3. The device of claim 2, wherein said notch passage disposed in angular relation to a longitudinal axis of said thread carrier.

4. The device of claim 2, wherein engagement of said first hook with said thread carrier external surface resiliently flexes said first resiliently flexible hook member, wherein resilient flexure moves said first hook through said notch passage.

5. The device of claim 4, further comprising a thread disposed in said aperture element of said thread carrier.

6. The device of claim 5, wherein slidable engagement of said thread carrier in relation to said first hook disposes said thread adjacent said first hook member prior to movement of said first hook through said notch passage, whereby passage of said first hook through said notch passage captures said thread by said first resiliently flexible hook member.

7. The device of claim 6, further comprising a second resiliently flexible hook member terminating in a second hook, said second resiliently flexible hook member disposed a distance from said first resiliently flexible hook member, said first hook overlapping said second hook, said first and second hooks correspondingly slidably engage opposite sides of said thread carrier.

8. The device of claim 1, wherein said thread carrier tapers approaching said thread carrier terminal end.

9. The device of claim 8, wherein said thread carrier tapers to a point approaching said thread carrier terminal end, said point capable of penetrating a substrate.

10. The device of claim 9, wherein said substrate comprises an animal tissue.

11. A method in a thread capture device, comprising:
disposing a notch in a thread carrier proximate a thread carrier terminal end;
disposing an aperture element in said thread carrier, said aperture element passing through and having a pair of openings disposed on opposite sides of said thread carrier, said aperture element disposed separate from and between said thread carrier terminal end and said notch; and
disposing a thread capturer in spatial relation to said thread carrier, said thread capturer having a first resiliently flexible hook member terminating in a first hook, said thread carrier moves to slidably engage said thread carrier external surface with said first hook, said hook aligning with and passing into a notch passage first end and out of a notch passage second end each open on said thread carrier external surface.

12. The method of claim 11, further comprising disposing a notch passage first end and a notch passage second end open on said tread carrier external surface to define a notch passage, said first hook adapted to pass through said notch passage.

13. The method of claim 12, further comprising disposing said notch passage in angular relation to a longitudinal axis of said thread carrier.

14. The method of claim 12, further comprising disposing a thread in said aperture element of said thread carrier.

15. The method of claim 14, further comprising disposing said aperture element in said thread carrier at a location which correspondingly disposes said thread adjacent said first resiliently flexible hook member prior to movement of said first hook through said notch passage, whereby passage of said first hook through said hook passage captures said thread by said first hook.

16. The method of claim 15, further comprising disposing a second resiliently flexible hook member a distance from said first resiliently flexible hook member, said second resiliently flexible hook member terminating in a second hook, said first hook overlapping said second hook, said first and second hooks correspondingly slidably engage opposite sides of said thread carrier.

17. The method of claim 11, further comprising disposing said first hook to flex said first resiliently flexible hook member upon engagement of said first hook with said thread carrier, whereby resilient flexure moves said first hook through said notch passage.

18. The method of claim 11, further comprising tapering said thread carrier approaching said thread carrier terminal end.

19. The method of claim 18, further comprising tapering said thread carrier to a point approaching said thread carrier terminal end, said point capable of penetrating a substrate.

20. The method of claim 19, wherein said substrate comprises an animal tissue.

21. A method in a thread capture device, comprising:
moving a tread carrier in relation to a thread capturer,
said thread carrier having:
a terminal end;
a notch disposed in a thread carrier external surface proximate said thread carrier terminal end;
an aperture element passing through and having a pair of openings disposed on opposite sides of said thread carrier, said aperture element disposed separate from and between said thread carrier terminal end and said notch,
said thread capturer having:
a first resiliently flexible hook member terminating in a first hook;
slidably engaging said thread carrier external surface to said first hook;
aligning said first hook with a notch disposed in said thread carrier;
passing said first hook into a notch first end and out of a notch second end each open on said thread carrier external surface; and
slidably disengaging said thread carrier from said first resiliently flexible hook member.

22. The method of claim 21, further comprising slidably engaging said thread carrier external surface to a second hook and slidably disengaging said thread carrier from said second resiliently flexible hook member.

23. The method of claim 22, further comprising resiliently flexing a first resiliently flexible hook member coupled to said first hook.

24. The method of claim 23, further comprising resiliently flexing a second resiliently flexible hook member coupled to said second hook.

25. The method of claim 24, further comprising overlapping said second hook and said first hook.

26. The method of claim 21, said thread carrier including an aperture element communicating between opposing sides of said thread carrier, further comprising disposing a thread in said aperture element and capturing said thread in said first hook.

27. The method of claim 21, further comprising penetrating animal tissue.

* * * * *